US010821239B2

(12) United States Patent
Hanson et al.

(10) Patent No.: US 10,821,239 B2
(45) Date of Patent: Nov. 3, 2020

(54) INSERTION MECHANISMS HAVING VENTED FLUID PATHWAYS FOR DRUG DELIVERY PUMPS

(71) Applicant: UNL Holdings LLC, New York, NY (US)

(72) Inventors: Ian B. Hanson, Wayne, PA (US); Paul F. Bente, IV, Wayne, PA (US); Sean M. O'Connor, West Chester, PA (US); Jaimin B. Shah, Philadelphia, PA (US)

(73) Assignee: UNL Holdings LLC, New York, NY (US)

( * ) Notice: Subject to any disclaimer, the term of this patent is extended or adjusted under 35 U.S.C. 154(b) by 315 days.

(21) Appl. No.: 14/413,120

(22) PCT Filed: Jul. 11, 2013

(86) PCT No.: PCT/US2013/050075
§ 371 (c)(1),
(2) Date: Jan. 6, 2015

(87) PCT Pub. No.: WO2014/011879
PCT Pub. Date: Jan. 16, 2014

(65) Prior Publication Data
US 2015/0190588 A1    Jul. 9, 2015

Related U.S. Application Data

(60) Provisional application No. 61/670,203, filed on Jul. 11, 2012.

(51) Int. Cl.
*A61M 5/36* (2006.01)
*A61M 5/158* (2006.01)
(Continued)

(52) U.S. Cl.
CPC .......... *A61M 5/36* (2013.01); *A61M 5/14244* (2013.01); *A61M 5/14248* (2013.01);
(Continued)

(58) Field of Classification Search
CPC .......... A61M 5/14244; A61M 5/14248; A61M 5/385; A61M 5/14224; A61M 2005/14252; A61M 2005/1585; A61M 2205/7536
See application file for complete search history.

(56) References Cited

U.S. PATENT DOCUMENTS 3,778,971 A * 12/1973 Granger ................. A61M 5/36
604/126
4,755,173 A * 7/1988 Konopka .......... A61M 25/0606
128/DIG. 26
(Continued)

FOREIGN PATENT DOCUMENTS

CN         1245077 A    2/2000
CN       101631585 A    1/2010
(Continued)

OTHER PUBLICATIONS

European Patent Office, etc. International Search Report and Written Opinion from PCT/US2013/050075 (dated Jan. 7, 2014), 18 pages.
(Continued)

*Primary Examiner* — Laura A Bouchelle
*Assistant Examiner* — Justin L Zamory
(74) *Attorney, Agent, or Firm* — Hamilton, Brook, Smith & Reynolds, P.C.

(57) ABSTRACT

An insertion mechanism having a vented fluid pathway includes an insertion biasing member 210, a hub 212, a needle 214, a retraction biasing member 216, and a manifold 240 having a septum 230 and a cannula 234, wherein the
(Continued)

annular space between the septum 230 and the cannula 234 defines a manifold header 242. The manifold and fluid conduit are ventable through the membrane prior to or just after needle 214 and cannula 234 are inserted into the user. Such insertion is caused by the insertion biasing member(s) 210, after which only the needle 214 or another occlusion element is retracted. Such retraction may open a fluid pathway from the manifold header 242 to the body through the cannula 234 and/or needle 214. A drug delivery pump 10 includes such an insertion mechanism 200 having a vented fluid pathway. The drug delivery pump 10 may contain the insertion mechanism 200 having a vented fluid pathway in either an internally i or an externally tethered configuration.

18 Claims, 14 Drawing Sheets

(51) Int. Cl.
*A61M 5/38* (2006.01)
*A61M 5/142* (2006.01)

(52) U.S. Cl.
CPC ............ *A61M 5/158* (2013.01); *A61M 5/385* (2013.01); *A61M 2005/14252* (2013.01); *A61M 2005/1585* (2013.01)

(56) References Cited

U.S. PATENT DOCUMENTS

| | | | | |
|---|---|---|---|---|
| 5,545,143 | A | * | 8/1996 | Fischell ................ A61M 5/158 604/180 |
| 2004/0069044 | A1 | | 4/2004 | Lavi et al. |
| 2007/0282269 | A1 | | 12/2007 | Carter et al. |
| 2010/0331824 | A1 | * | 12/2010 | Moberg .............. A61M 5/1413 604/533 |
| 2011/0054390 | A1 | | 3/2011 | Searle et al. |
| 2011/0306929 | A1 | * | 12/2011 | Levesque .............. A61M 5/322 604/150 |
| 2013/0060226 | A1 | * | 3/2013 | Fini ....................... A61M 5/162 604/500 |

FOREIGN PATENT DOCUMENTS

| | | |
|---|---|---|
| CN | 101947337 A | 1/2011 |
| JP | S62-201159 A | 9/1987 |
| JP | 2002-529204 A | 9/2002 |
| JP | 2007511325 A | 5/2007 |
| JP | 2010-501281 A | 1/2010 |
| JP | 2011-506007 A | 3/2011 |
| WO | WO 00/29049 A1 | 5/2000 |
| WO | 2005/049117 A2 | 6/2005 |
| WO | WO 2008/024810 A2 | 2/2008 |
| WO | WO 2009/039013 A1 | 3/2009 |
| WO | WO 2009/077091 A1 | 6/2009 |
| WO | WO 2011/121023 A1 | 10/2011 |
| WO | 2014/011879 A1 | 1/2014 |

OTHER PUBLICATIONS

Notification Concerning Transmittal of International Preliminary Report on Patentability for International Application No. PCT/US2013/050075, "Insertion Mechanisms Having Vented Fluid Pathways for Drug Delivery Pumps", dated Jan. 22, 2015.

* cited by examiner

INSERTION MECHANISMS HAVING VENTED FLUID PATHWAYS FOR DRUG DELIVERY PUMPS

CROSS-REFERENCE TO RELATED APPLICATIONS

This application claims priority to U.S. Provisional Application No. 61/670,203, filed on Jul. 11, 2012, which is included by reference herein in its entirety for all purposes.

FIELD

THIS INVENTION relates to drug delivery pumps. More particularly, this invention relates to insertion mechanisms for drug delivery pumps, drug delivery pumps with safety integrated insertion mechanisms, the methods of operating such devices, and the methods of assembling such devices.

BACKGROUND

Parenteral delivery of various drugs, i.e., delivery by means other than through the digestive track, has become a desired method of drug delivery for a number of reasons. This form of drug delivery by injection may enhance the effect of the substance being delivered and ensure that the unaltered medicine reaches its intended site at a significant concentration. Similarly, undesired side effects associated with other routes of delivery, such as systemic toxicity, can potentially be avoided through parenteral delivery. By bypassing the digestive system of a mammalian patient, one can avoid degradation of the active ingredients caused by the catalytic enzymes in the digestive tract and liver and ensure that a necessary amount of drug, at a desired concentration, reaches the targeted site.

Traditionally, manually operated syringes and injection pens have been employed for delivering parenteral drugs to a patient. More recently, parenteral delivery of liquid medicines into the body has been accomplished by administering bolus injections using a needle and reservoir, continuously by gravity driven dispensers, or via transdermal patch technologies. Bolus injections often imperfectly match the clinical needs of the patient, and usually require larger individual doses than are desired at the specific time they are given. Continuous delivery of medicine through gravity-feed systems compromises the patient's mobility and lifestyle, and limits the therapy to simplistic flow rates and profiles. Another form of drug delivery, transdermal patches, similarly has its restrictions. Transdermal patches often require specific molecular drug structures for efficacy, and the control of the drug administration through a transdermal patch is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. Currently available ambulatory infusion devices are expensive, difficult to program and prepare for infusion, and tend to be bulky, heavy and very fragile. Filling these devices can be difficult and require the patient to carry both the intended medication as well as filling accessories. The devices often require specialized care, maintenance, and cleaning to assure proper functionality and safety for their intended long-term use, and are not cost-effective for patients or healthcare providers.

As compared to syringes and injection pens, pump type delivery devices can be significantly more convenient to a patient, in that doses of the drug may be calculated and delivered automatically to a patient at any time during the day or night. Furthermore, when used in conjunction with metabolic sensors or monitors, pumps may be automatically controlled to provide appropriate doses of a fluidic medium at appropriate times of need, based on sensed or monitored metabolic levels. As a result, pump type delivery devices have become an important aspect of modern medical treatments of various types of medical conditions, such as diabetes, and the like.

While pump type delivery systems have been utilized to solve a number of patient needs, manually operated syringes and injection pens often remain a preferred choice for drug delivery as they now provide integrated safety features and can easily be read to identify the status of drug delivery and the end of dose dispensing. However, manually operated syringes and injections pens are not universally applicable and are not preferred for delivery of all drugs. There remains a need for an adjustable (and/or programmable) infusion system that is precise and reliable and can offer clinicians and patients a small, low cost, light weight, simple to use alternative for parenteral delivery of liquid medicines.

SUMMARY

The embodiments of the present invention provide insertion mechanisms having vented fluid pathways, and pump-type drug delivery systems which includes such vented fluid pathways, which are capable of being primed to reduce or eliminate gaseous fluids from the fluid pathway system prior to introduction of a liquid fluid to a user. When delivering fluid subcutaneously or intramuscularly, it is important to minimize or eliminate the amount of gaseous fluid that is delivered into the user. Delivery of gaseous fluids, such as air or inert gases, is correlated to increased perception of pain for patients and may adversely affect absorption profiles of pharmaceutical treatments. As such, it is important to minimize or eliminate such gaseous fluids from the system prior to injection of the drug. While this is an important and desirable feature of drug delivery devices, such features should not be cumbersome or complicated for the user. The inventors of the present invention have developed a system which enables the reduction or elimination of gaseous fluids from the fluid pathway, but yet is easy to use for clinicians and patients.

In a first embodiment, the present invention provides an insertion mechanism having a vented fluid pathway which includes: one or more insertion biasing members, a hub, a needle, a refraction biasing member, and a manifold having a septum, a cannula, a manifold intake, and a membrane, wherein the annular space within the manifold between the septum, the cannula, the manifold intake, and the membrane defines a manifold header, wherein the manifold is configured to vent a gaseous fluid through the membrane and fill with a liquid fluid for delivery to the user through the cannula. The manifold intake is capable of connection with a fluid conduit. The insertion mechanism may be configured to be internally mounted within a drug pump or externally tethered to a drug pump by a conduit. In at least one embodiment, the vented or ventable insertion mechanism comprises two insertion biasing members. The septum closes the upper portion of the manifold while allowing the needle to pass through it. Another opening from the manifold is at least temporarily blocked by the needle as it resides within the cannula and/or another occlusion element such as a ferrule or plug, prior to operation of the insertion mechanism. The manifold intake receives fluid flow from the fluid conduit. The only remaining opening from manifold is blocked by membrane until operation of the insertion mechanism.

The membrane may be a number of filtering membranes which are capable of permitting passage of gaseous fluids but prohibiting passage of liquid fluids. For example, the membrane may be a permeable membrane or a semipermeable membrane. Additionally, the membrane may be or function as a sterile barrier. In at least one embodiment, the membrane is a permeable membrane selected from the group consisting of polyethylene terephthalate (PET), polytetrafluoroethylene (PTFE), one or more styrenes, and polyethylene fibers, and the combinations thereof. The membrane may be a separate component or be an integrated portion, such as part of the wall, of the manifold.

The insertion mechanism having a vented fluid pathway may further include a sensor. The sensor may be any number of sensors known to an ordinarily skilled artisan, such as those selected from the group consisting of pressure sensors, fluid sensors, optical sensors, mechanical sensors, electrical sensors, and electro-mechanical sensors, and the combinations thereof.

In another embodiment, the present invention provides a drug delivery pump which includes a housing and an assembly platform, upon which an activation mechanism, a drive mechanism, a fluid pathway connection, a power and control system, and an insertion mechanism having a vented fluid pathway may be mounted. The insertion mechanism having vented fluid pathway may be as described above. In a preferred embodiment, the drug pump utilizes a vented or ventable insertion mechanism having a vented fluid pathway which includes: one or more insertion biasing members, a hub, a needle, a refraction biasing member, and a manifold having a septum, a cannula, a manifold intake, and a membrane, wherein the annular space within the manifold between the septum, the cannula, the manifold intake, and the membrane defines a manifold header, wherein the manifold is configured to vent a gaseous fluid through the membrane and fill with a liquid fluid for delivery to the user through the cannula. The manifold intake is capable of connection with a fluid conduit. The insertion mechanism may be configured to be internally mounted within a drug pump or externally tethered to a drug pump by a conduit. In at least one embodiment, the vented or ventable insertion mechanism comprises two insertion biasing members.

In yet another embodiment of the present invention, a method of operating the insertion mechanism having a vented fluid pathway includes the steps of: (i.) initially maintaining a needle in a first position wherein fluid passage from a manifold header of a manifold through the cannula is blocked; (ii.) activating the flow of liquid drug fluid from a drug container through a fluid conduit to the manifold header of the manifold; (iii.) venting a gaseous fluid through a membrane within the manifold while prohibiting passage of the liquid drug fluid through the membrane; (iv.) activating an insertion biasing member to translate the needle and the cannula from the first position to a second position within a body of a user; and (v.) activating a retraction biasing member to translate the needle from the second position to a third position, wherein the third position permits passage of the liquid drug fluid from the manifold header of the manifold through the cannula and into the body of the user. In at least one embodiment, the step of activating an insertion biasing member to translate the needle and the cannula from the first position to a second position occurs after the step of venting a gaseous fluid through a membrane within the manifold. In another embodiment, the step of activating an insertion biasing member to translate the needle and the cannula from the first position to a second position may occur before the step of venting a gaseous fluid through a membrane within the manifold such that venting through the membrane is permitted only once the needle is in the second position. In such an embodiment, the step of activating an insertion biasing member to translate the needle and the cannula from the first position to a second position may cause the removal of a covering element from the membrane outside of the manifold to permit venting of any gaseous fluid from the fluid pathway. The covering element may be, for example, a cover, sheath, or sleeve. In either embodiment, however, the passage of the liquid drug fluid is permitted to occur only after the venting step and upon translation of the needle from the second position to a third position, wherein the third position permits passage of the liquid drug fluid from the manifold header of the manifold through the cannula and into the body of the user. In yet another embodiment, the method further includes, prior to the step of activating a retraction biasing member to translate the needle from the second position to a third position, the step of: measuring by a sensor the substantial completion of venting the gaseous fluid through the membrane.

Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present invention may include one or more additional components which may be considered standard components in the industry of medical devices. The components, and the embodiments containing such components, are within the contemplation of the present invention and are to be understood as falling within the breadth and scope of the present invention.

BRIEF DESCRIPTION OF THE DRAWINGS

The following non-limiting embodiments of the invention are described herein with reference to the following drawings, wherein.

DETAILED DESCRIPTION

Figure 1A:
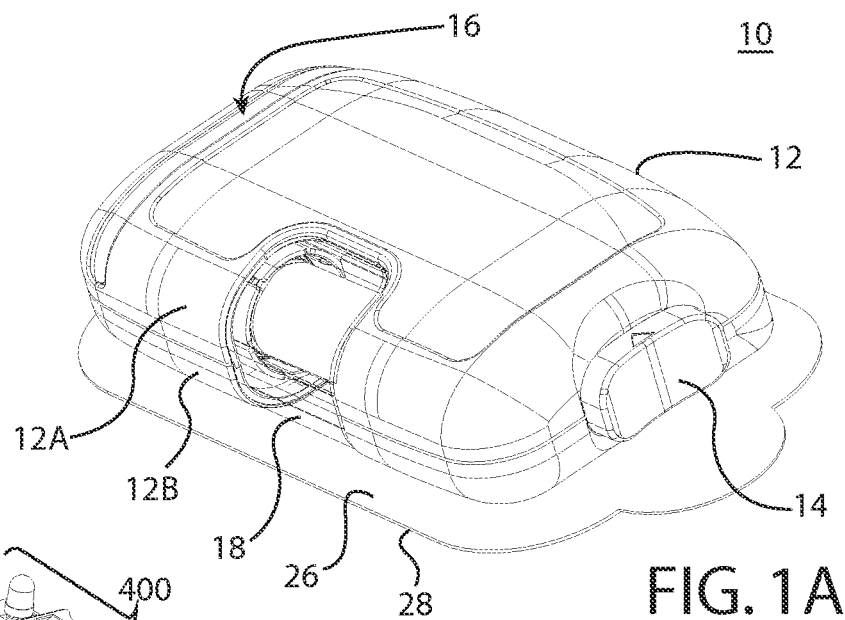
FIG. 1A shows an isometric view of a drug delivery pump having safety integrated insertion mechanisms, according to one embodiment of the present invention.

When delivering drug fluid to a user, such as by subcutaneous or intramuscular injection, it is important to minimize or eliminate the amount of gaseous fluid that is delivered into the user. Delivery of gaseous fluids, such as air or inert gases, is correlated to increased perception of pain for patients and may adversely affect absorption profiles of pharmaceutical treatments. As such, it is important to minimize or eliminate such gaseous fluids from the system prior to injection of the drug. While this is an important and desirable feature of drug delivery devices, such features should not be cumbersome or complicated for the user. The inventors of the present invention have developed a system which enables the reduction or elimination of gaseous fluids from the fluid pathway, but yet is easy to use for clinicians and patients.

As used herein to describe the insertion mechanisms, drug delivery pumps, or any of the relative positions of the components of the present invention, the terms "axial" or "axially" refer generally to a longitudinal axis "A" around which the insertion mechanisms are preferably positioned, although not necessarily symmetrically there-around. The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D". As used herein, the term "glass" should be understood to include other similarly non-reactive materials suitable for use in a pharmaceutical grade application that would normally require glass, including but not limited to certain non-reactive polymers such as cyclic olefin copolymers (COC) and cyclic olefin polymers (COP). The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. "Fluid" refers primarily to liquids, but can also include suspensions of solids dispersed in liquids, and gasses dissolved in or otherwise present together within liquids inside the fluid-containing portions of syringes. According to various aspects and embodiments described herein, reference is made to a "biasing member", such as in the context of one or more biasing members for insertion or retraction of the needle, trocar, and/or cannula. It will be appreciated that the biasing member may be any member that is capable of storing and releasing energy. Non-limiting examples include a spring, such as for example a coiled spring, a compression or extension spring, a torsional spring, and a leaf spring, a resiliently compressible or elastic band, or any other member with similar functions. In at least one embodiment of the present invention, the biasing member is a spring, preferably a compression spring.

Figure 1B:
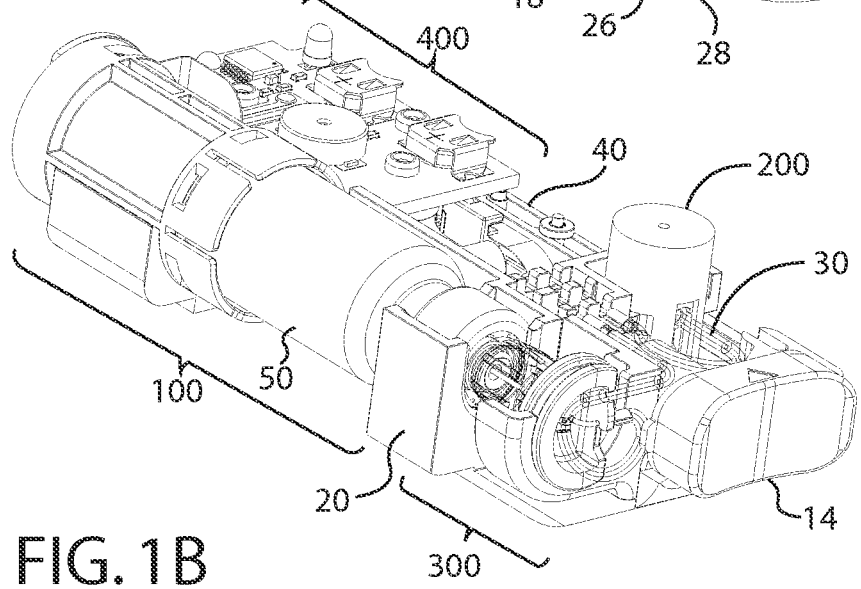
FIG. 1B shows an isometric view of the interior components of the drug delivery pump shown in FIG. 1A.
Figure 1C:
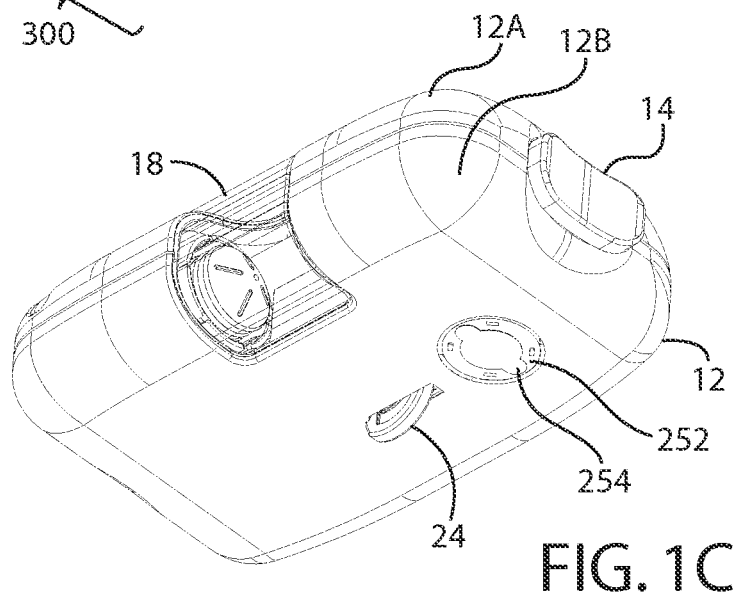
FIG. 1C shows an isometric view of the bottom of the drug delivery pump shown in FIG. 1A.
Figure 2:
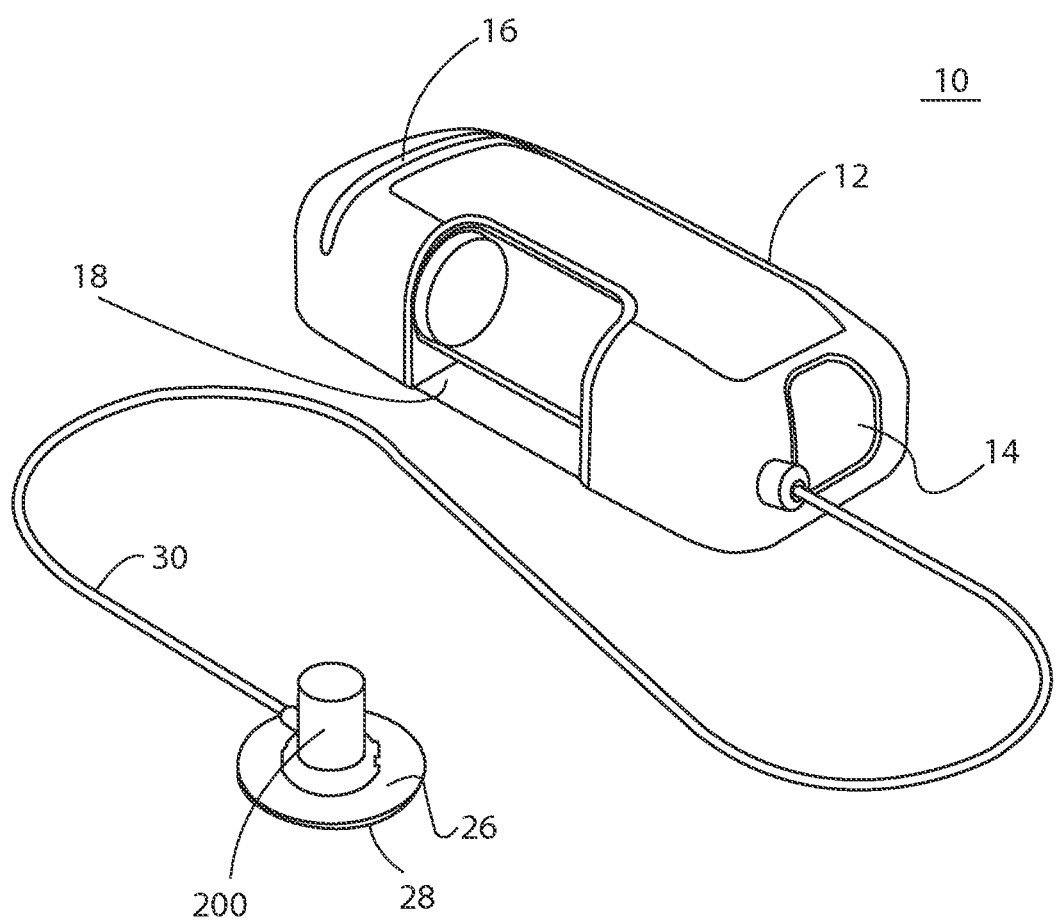
FIG. 2 shows an isometric view of a drug delivery pump having a tethered insertion mechanism, according to another embodiment of the present invention.

The present invention relates to vented fluid pathway systems having a membrane, such as a permeable or semi-permeable membrane, and drug delivery pumps which utilize such vented fluid pathway systems for the parenteral delivery of drug fluids. Such novel components and devices provide a mechanism to prime (e.g., the evacuation or removal of air or other gaseous fluid) the fluid pathway prior to injection and dosing of the drug treatment. The novel systems and devices of the present invention can be employed in a number of different configurations, and can be utilized with both pre-filled cartridges and fill-at-time-of-use primary drug containers. FIGS. 1A-1C show isometric views of one embodiment of the present invention in which the fluid pathway is internal to the drug delivery pump. FIG. 2 shows an isometric view of another embodiment of the present invention in which the fluid pathway is at least partially external to the drug delivery pump in a tethered configuration. Both of these embodiments of the present invention allow patients to deliver any volume of drug fluid without the need to maintain needle contact manually. This may be a particularly useful aspect for the delivery of large volumes of drug fluids, since it may alleviate the need for multiple manual injections and/or prolonged patient inactivity during drug delivery. Additionally, both of these embodiments of the present invention may utilize and provide a mechanism to prime the fluid pathway prior to injection and dosing of the drug treatment. Additionally, such devices are safe and easy to use, and are aesthetically and ergonomically appealing for self-administering patients. The devices described herein incorporate features which make activation, operation, and lock-out of the device simple for even untrained users. The novel devices of the present invention provide these desirable features without any of the problems associated with known prior art devices. Certain non-limiting embodiments of the novel drug delivery pump, insertion mechanism, and their respective components are described further herein with reference to the accompanying figures.

Drug Delivery Pump:

As used herein, the term "pump" is intended to include any number of drug delivery systems which are capable of dispensing a fluid to a user upon activation. Such drug delivery systems include, for example, injection systems, infusion pumps, bolus injectors, and the like. FIGS. 1A-1C show an exemplary drug delivery device according to at least one embodiment of the present invention. The drug delivery device may be utilized to administer delivery of a drug treatment into a body of a user. As shown in FIGS. 1A-1C, the drug delivery pump 10 includes a pump housing 12. Pump housing 12 may include one or more housing subcomponents which are fixedly engageable to facilitate easier manufacturing, assembly, and operation of the drug pump. For example, drug delivery pump 10 includes a pump housing 12 which includes an upper housing 12A and a lower housing 12B. The drug pump may further include an activation mechanism 14, a status indicator 16, and a window 18. Window 18 may be any translucent or transmissive surface through which the operation of the drug pump may be viewed. As shown in FIG. 1B, drug pump further includes assembly platform 20, sterile fluid conduit 30, drive mechanism 100 having drug container 50, insertion mechanism 200, fluid pathway connection 300, and power and control system 400. One or more of the components of such drug pumps may be modular in that they may be, for example, pre-assembled as separate components and configured into position onto the assembly platform 20 of the drug delivery pump 10 during manufacturing.

The pump housing 12 contains all of the device components and provides a means of removably attaching the drug delivery pump 10 to the skin of the user. The pump housing 12 also provides protection to the interior components of the drug delivery pump 10 against environmental influences. The pump housing 12 is ergonomically and aesthetically designed in size, shape, and related features to facilitate easy packaging, storage, handling, and use by users who may be untrained and/or physically impaired. Furthermore, the external surface of the pump housing 12 may be utilized to provide product labeling, safety instructions, and the like. Additionally, as described above, housing 12 may include certain components, such as status indicator 16 and window 18, which may provide operation feedback to the user.

In at least one embodiment, the drug delivery pump 10 provides an activation mechanism 14 that is displaced by the user to trigger the start command to the power and control system 400. In a preferred embodiment, the activation mechanism is a start button 14 that is located through the pump housing 12, such as through an aperture between upper housing 12A and lower housing 12B, and which contacts a control arm 40 of the power and control system 400. In at least one embodiment, the start button 14 may be a push button, and in other embodiments, may be an on/off switch, a toggle, or any similar activation feature known in the art. The pump housing 12 also provides a status indicator 16 and a window 18. In other embodiments, one or more of the activation mechanism 14, the status indicator 16, the window 18, and combinations thereof may be provided on the upper housing 12A or the lower housing 12B such as, for example, on a side visible to the user when the drug delivery pump 10 is placed on the body of the user. Housing 12 is described in further detail hereinafter with reference to other components and embodiments of the present invention.

Drug pump is configured such that, upon activation by a user by depression of the activation mechanism, the drug pump is initiated to: insert a fluid pathway into the user; enable, connect, or open necessary connections between a drug container, a fluid pathway, and a sterile fluid conduit; and force drug fluid stored in the drug container through the fluid pathway and fluid conduit for delivery into a user. One or more optional safety mechanisms may be utilized, for example, to prevent premature activation of the drug pump. For example, an optional on-body sensor 24 (shown in FIG. 1C) may be provided in one embodiment as a safety feature to ensure that the power and control system 400, or the activation mechanism, cannot be engaged unless the drug delivery pump 10 is in contact with the body of the user. In one such embodiment, the on-body sensor 24 is located on the bottom of lower housing 12B where it may come in contact with the user's body. Upon displacement of the on-body sensor 24, depression of the activation mechanism is permitted. Accordingly, in at least one embodiment the on-body sensor 24 is a mechanical safety mechanism, such as for example a mechanical lock out, that prevents triggering of the drug delivery pump 10 by the activation mechanism 14. In another embodiment, the on-body sensor may be an electro-mechanical sensor such as a mechanical lock out that sends a signal to the power and control system 400 to permit activation. In still other embodiments, the on-body sensor can be electrically based such as, for example, a capacitive- or impedance-based sensor which must detect tissue before permitting activation of the power and control system 400. These concepts are not mutually exclusive and one or more combinations may be utilized within the breadth of the present invention to prevent, for example, premature activation of the drug pump. In a preferred embodiment, the drug delivery pump 10 utilizes one or more mechanical on-body sensors. Additional integrated safety mechanisms are described herein with reference to other components of the novel drug pumps.

FIG. 2 provides another embodiment of the drug delivery pump 10, in which the insertion mechanism 200 is tethered to the main body of the drug pump by a conduit 30. Such an embodiment may be desirable, for example, when the drug delivery pump 10 is worn on a belt or in the pocket of the user and the insertion mechanism 200 alone is temporarily attached, such as by an adhesive patch 26, to the user's body. The embodiment of the drug pump shown in FIG. 2 is similar to that which is shown in FIGS. 1A-1C, except that the conduit 30 extends at least partly outside of the pump housing 12 to connect to a tethered external insertion mechanism 200. The same insertion mechanism 200 and remaining components of the drug pump may be utilized by any of the drug pump embodiments described herein regardless of whether such components are internal or external to the drug pump housing. Such components may include, for example, a power and control system, a fluid pathway connection, a drive mechanism, and an insertion mechanism, as detailed further herein.

Power and Control System:

The power and control system 400 includes a power source, which provides the energy for various electrical components within the drug pump, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system 400 controls several device interactions with the user and interfaces with the drive mechanism 100. In one embodiment, the power and control system 400 interfaces with the control arm 40 to identify when the on-body sensor 24 and/or the activation mechanism 14 have been activated. The power and control system 400 may also interface with the status indicator 16 of the pump housing 12, which may be a transmissive or translucent material which permits light transfer, to provide visual feedback to the user. The power and control system 400 interfaces with the drive mechanism 100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug pump are not engaged or connected until activation by the user. This is a desirable safety feature that prevents accidental operation of the drug pump and may additionally maintain the energy contained in the power source during storage, transportation, and the like.

The power and control system 400 may be configured to provide a number of different status indicators to the user. For example, the power and control system 400 may be configured such that after the on-body sensor and/or trigger mechanism have been pressed, the power and control system 400 provides a ready-to-start status signal via the status indicator 16 if device start-up checks provide no errors. After providing the ready-to-start status signal and, in an embodiment with the optional on-body sensor, if the on-body sensor remains in contact with the body of the user, the power and control system 400 will power the drive mechanism 100 to begin delivery of the drug treatment through the fluid pathway connection 300 and sterile fluid conduit 30. In a preferred embodiment of the present invention, the insertion mechanism 200 and the fluid pathway connection 300 may be caused to activate directly by user operation of the activation mechanism 14. During the drug delivery process, the power and control system 400 is configured to provide a dispensing status signal via the status indicator 16. After the drug has been administered into the body of the user and after the end of any additional dwell time, to ensure that substantially the entire dose has been delivered to the user, the power and control system 400 may provide an okay-to-remove status signal via the status indicator 16. This may be independently verified by the user by viewing the drive mechanism and drug dose delivery through the window 18 of the pump housing 12. Additionally, the power and control system 400 may be configured to provide one or more alert signals via the status indicator 16, such as for example alerts indicative of fault or operation failure situations.

Other power and control system configurations may be utilized with the novel drug pumps of the present invention. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism 14 of the drug delivery pump 10 prior to drug pump activation. Additionally, the system may include a feature which permits the user to respond to the end-of-dose signals and to deactivate or power-down the drug pump. Such a feature may similarly require a delayed depression of the activation mechanism, to prevent accidental deactivation of the device. Such features provide desirable safety integration and ease-of-use parameters to the drug pumps. An additional safety feature may be integrated into the activation mechanism to prevent partial depression and, therefore, partial activation of the drug pumps. For example, the activation mechanism and/or power and control system may be configured such that the device is either completely off or completely on, to prevent partial activation. Such features are described in further detail hereinafter with regard to other aspects of the novel drug pumps.

Fluid Pathway Connection:

A number of fluid pathway connections may be utilized within the embodiments of the present invention. Generally, a suitable fluid pathway connection includes a sterile fluid conduit, a piercing member, and a sterile sleeve attached to a drug container or a sliding pierceable seal integrated within a drug container. The fluid pathway connection may further include one or more flow restrictors. Upon proper activation of the drug delivery pump 10, the fluid pathway connection 300 is enabled to connect the sterile fluid conduit 30 to the drug container of the drive mechanism 100. Such connection may be facilitated by a piercing member, such as a needle, penetrating a pierceable seal of the drug container of the drive mechanism 100. The sterility of this connection may be maintained by performing the connection within a flexible sterile sleeve. Upon substantially simultaneous activation of the insertion mechanism, the fluid pathway between drug container and insertion mechanism is complete to permit drug delivery into the body of the user.

In at least one embodiment of the present invention, the piercing member of the fluid pathway connection is caused to penetrate the pierceable seal of the drug container of the drive mechanism by direct action of the user, such as by depression of the activation mechanism by the user. For example, the activation mechanism itself may bear on the fluid pathway connection such that displacement of the activation mechanism from its original position also causes displacement of the fluid pathway connection. In one such embodiment, the fluid pathway connection may be substantially similar to that described in International Patent Application No. PCT/US2012/054861, which is included by reference herein in its entirety for all purposes. According to such an embodiment, the connection is enabled by the user depressing the activation mechanism and, thereby, driving the piercing member through the pierceable seal, because this prevents fluid flow from the drug container until desired by the user. In such an embodiment, a compressible sterile sleeve may be fixedly attached between the cap of the drug container and the connection hub of the fluid pathway connection. The piercing member may reside within the sterile sleeve until a connection between the fluid connection pathway and the drug container is desired. The sterile sleeve may be sterilized to ensure the sterility of the piercing member and the fluid pathway prior to activation.

Alternatively, the fluid pathway connection may be integrated into a drug container as described in International Patent Application No. PCT/US2013/030478, for example, which is included by reference herein in its entirety for all purposes. According to such an embodiment, a drug container may have a drug chamber within a barrel between a sliding pierceable seal and a plunger seal. A drug fluid is contained in the drug chamber. Upon activation of the device by the user, a drive mechanism asserts a force on a plunger seal contained in the drug container. As the plunger seal asserts a force on the drug fluid, pneumatic pressure builds by compression of the drug fluid and the force is relayed to the sliding pierceable seal. The sliding pierceable seal is caused to slide towards the cap, causing it to be pierced by the piercing member retained within the integrated sterile fluid pathway connection. Accordingly, the integrated sterile fluid pathway connection is connected (i.e., the fluid pathway is opened) by the pneumatic force of the drug fluid within the drug chamber created by activation of a drive mechanism. Once the integrated sterile fluid pathway connection is connected or opened, drug fluid is permitted to flow from the drug container, through the integrated sterile fluid pathway connection, sterile fluid conduit, and insertion mechanism, and into the body of the user for drug delivery. In at least one embodiment, the fluid flows through only a manifold and a cannula and/or needle of the insertion mechanism, thereby maintaining the sterility of the fluid pathway before and during drug delivery.

Regardless of the fluid pathway connection utilized by the drug pump, the drug pump is capable of delivering a range of drugs with different viscosities and volumes. The drug pump is capable of delivering a drug at a controlled flow rate (speed) and/or of a specified volume. In one embodiment, the drug delivery process is controlled by one or more flow restrictors within the fluid pathway connection and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connection 300 and the sterile fluid conduit 30 are provided hereinafter in later sections in reference to other embodiments.

Drive Mechanism:

A number of drive mechanisms may be utilized to force fluid from a drug container for delivery into the body of a user. In one such embodiment, the drive mechanism 100 may be substantially similar to that described in International Patent Application No. PCT/US2012/053241, which is included by reference herein in its entirety for all purposes. In at least one embodiment, the drive mechanism 100 includes drug container 50 having a cap, a pierceable seal, and a plunger seal. The drug container may contain a drug fluid, within the container between the cap and the plunger seal, for delivery through the insertion mechanism and drug pump into the body of the user. The drive mechanism may further include one or more drive biasing members, one or more release mechanisms, and one or more guides. The components of the drive mechanism function to force a fluid from the drug container out through the pierceable seal or, preferably, through the piercing member of the fluid pathway connection for delivery through the fluid pathway connection, sterile fluid conduit, and insertion mechanism into the body of the user.

The drive mechanism may further include one or more electrical contacts located on corresponding components which, upon contact between electrical contacts, are capable of continuing an energy pathway or otherwise relay a signal to and/or from the power and control system 400. Such signals may be transferred across one or more interconnects. Such components may be utilized within the drive mechanism to measure and relay information related to the status of operation of the drive mechanism, which may be converted by the power and control system 400 into tactile, auditory, and/or visual feedback to the user.

In one particular embodiment, the drive mechanism 100 employs one or more compression springs as the biasing member(s). Upon activation of the drug pump by the user, the power and control system may be actuated to directly or indirectly release the compression spring(s) from an energized state. Upon release, the compression spring(s) may bear against and act upon the plunger seal to force the fluid drug out of the drug container. The fluid pathway connection is connected through the pierceable seal prior to, concurrently with, or after activation of the drive mechanism to permit fluid flow from the drug container, through the fluid pathway connection, sterile fluid conduit, and insertion mechanism, and into the body of the user for drug delivery. In at least one embodiment, the fluid flows through only a manifold and a cannula of the insertion mechanism, thereby maintaining the sterility of the fluid pathway before and during drug delivery. Such components and their functions are described in further detail hereinafter.

Figure 3A:
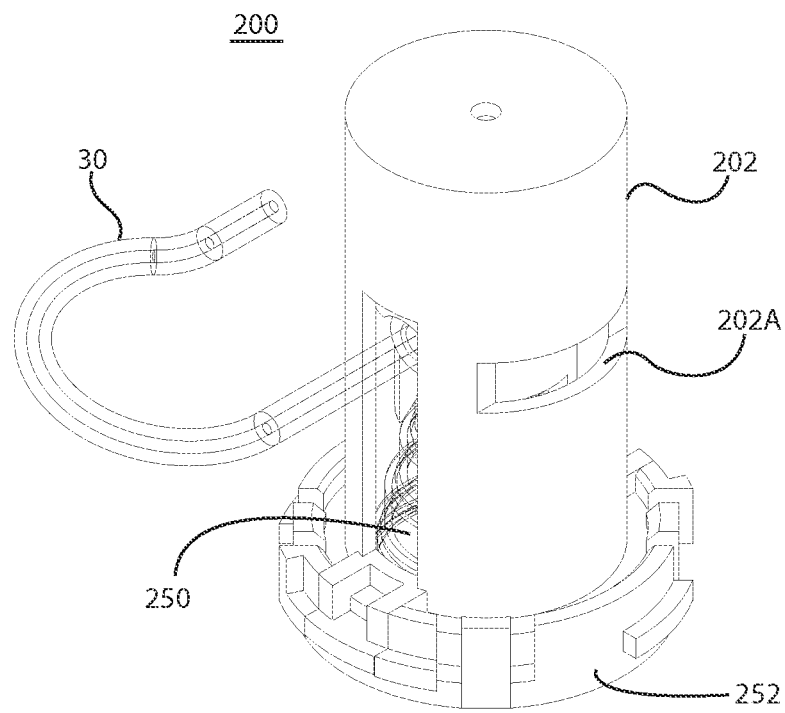
FIG. 3A shows an isometric view of an insertion mechanism, according to a first embodiment of the present invention.
Figure 3B:
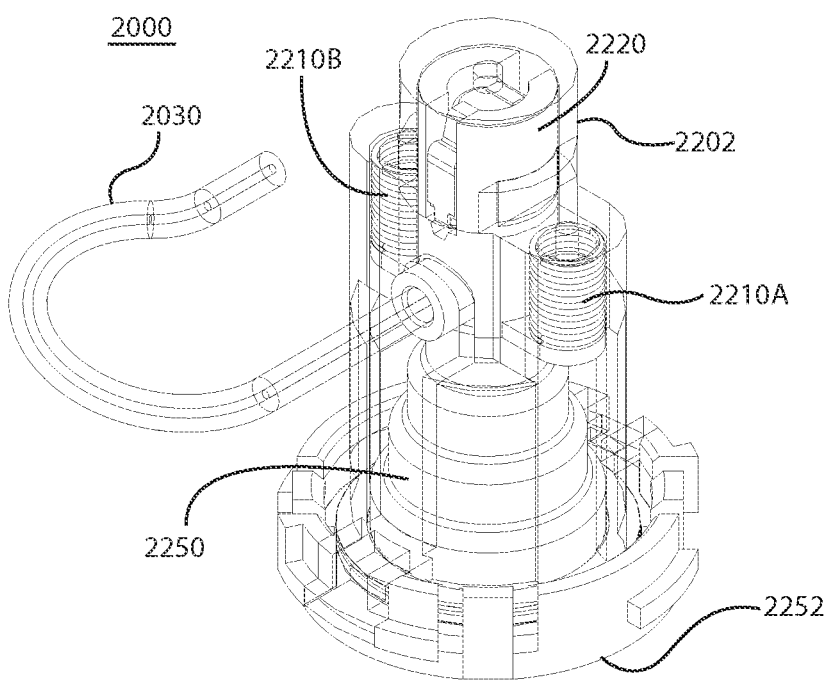
FIG. 3B shows an isometric view of an insertion mechanism, according to another embodiment of the present invention.

Insertion Mechanism:

The pump-type delivery devices of the present invention may be connected in fluid flow communication to a patient or user, for example, through any suitable hollow tubing. A solid bore needle may be used to pierce the skin of the patient and place a hollow cannula at the appropriate delivery position, with the solid bore needle being removed or retracted prior to drug delivery to the patient. As stated above, the fluid can be introduced into the body through any number of means, including but not limited to: an automatically inserted needle, cannula, micro-needle array, or infusion set tubing. A number of mechanisms may also be employed to activate the needle insertion into the patient. For example, a single spring insertion mechanism (as shown in FIG. 3A) or a dual spring insertion mechanism (as shown in FIG. 3B) may be employed to provide sufficient force to cause the needle and cannula to pierce the skin of the patient. The same spring, an additional spring, or another similar mechanism may be utilized to retract the needle from the patient. In a preferred embodiment, the insertion mechanism may generally be as described in International Patent Application No. PCT/US2012/53174, which is included by reference herein in its entirety for all purposes. Such a configuration may be utilized for insertion of the drug delivery pathway into, or below, the skin (or muscle) of the patient in a manner that minimizes pain to the patient. Other known methods for insertion of a fluid pathway may be utilized and are contemplated within the bounds of the present invention.

Figure 4A:
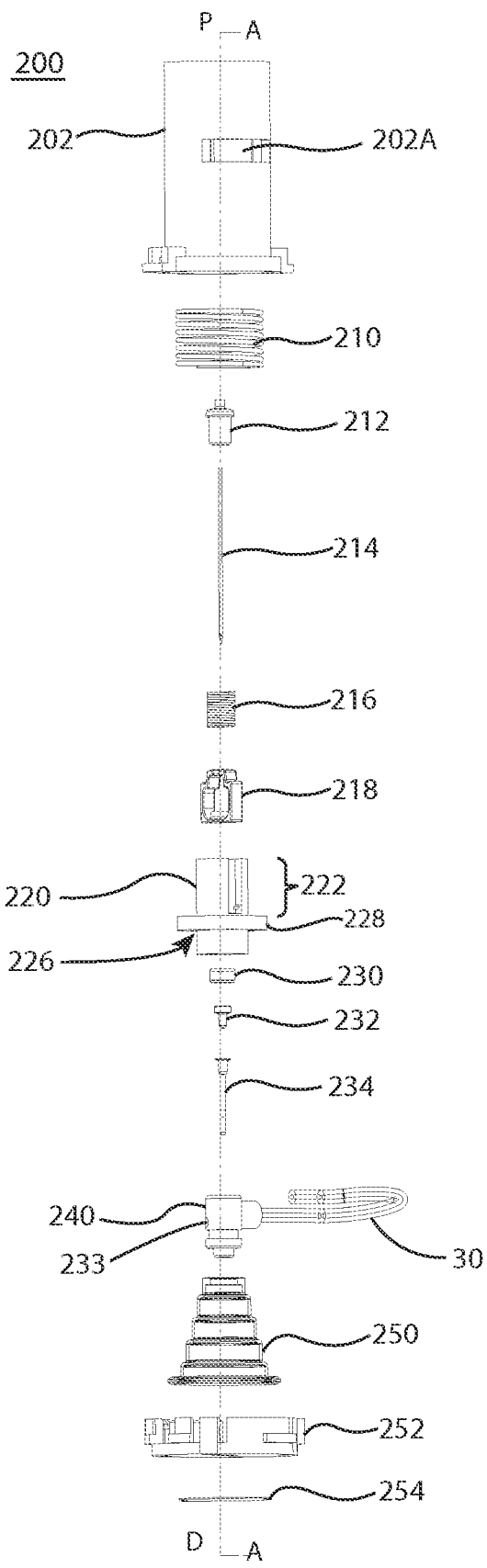
FIG. 4A shows an exploded view, exploded along an axis "A," of the insertion mechanism shown in FIG. 3A.
Figure 4B:
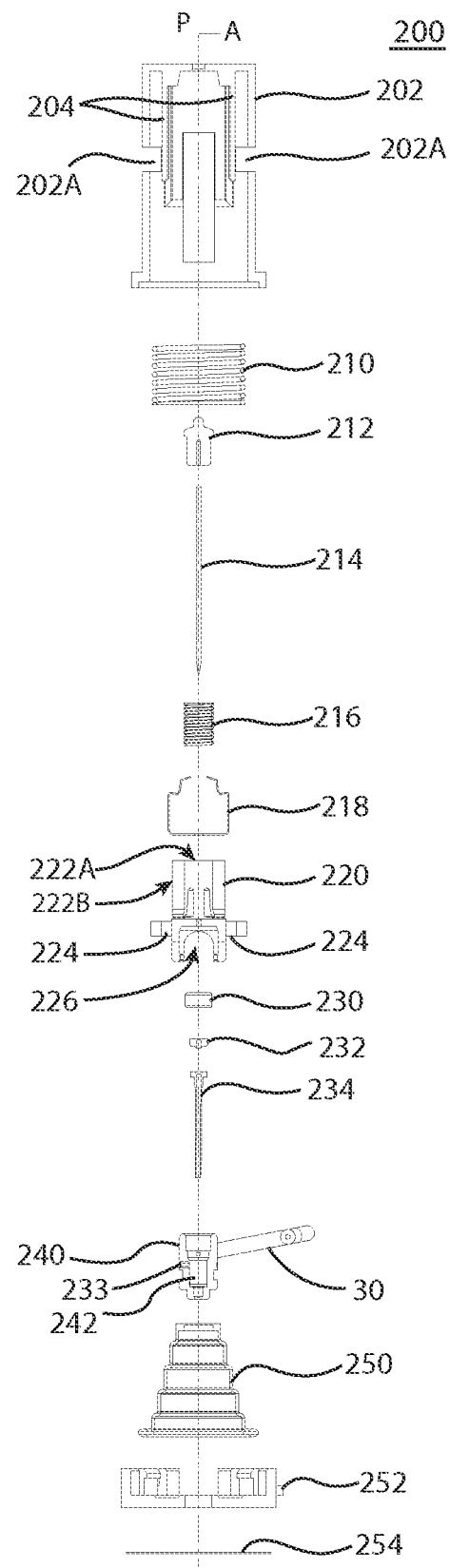
FIG. 4B shows a cross-sectional exploded view, exploded along an axis "A," of the insertion mechanism shown in FIG. 3A.

In a first embodiment, the present invention provides a fluid pathway system that allows a tube, conduit, or other fluid channel to be evacuated of air (or another gaseous fluid) prior to operation. In one such embodiment, the ventable fluid pathway system is integrated into an insertion mechanism 200. The insertion mechanism includes an insertion mechanism housing 202 having one or more lockout windows 202A, a base 252, and a sterile boot 250, as shown in FIG. 4A. Base 252 may be connected to assembly platform 20 to integrate the insertion mechanism into the drug delivery pump 10 (as shown in FIG. 1B). The connection of the base 252 to the assembly platform 20 may be, for example, such that the bottom of the base is permitted to pass-through a hole in the assembly platform to permit direct contact of the base to the body of the user. In such configurations, the bottom of the base 252 may include a sealing membrane 254 that, at least in one embodiment, is removable prior to use of the drug delivery pump 10. Alternatively, the sealing membrane 254 may remain attached to the bottom of the base 252 such that the needle 214 pierces the sealing membrane 254 during operation of the drug delivery pump 10. As shown in FIGS. 4A and 4B, the insertion mechanism 200 may further include an insertion biasing member 210, a hub 212, a needle 214, a retraction biasing member 216, a clip 218, a manifold guide 220, a septum 230, a cannula 234, and a manifold 240. The manifold 240 may connect to fluid conduit 30 to permit fluid flow through the manifold 240, cannula 234, and into the body of the user during drug delivery, as will be described in further detail herein.

Figure 5A:
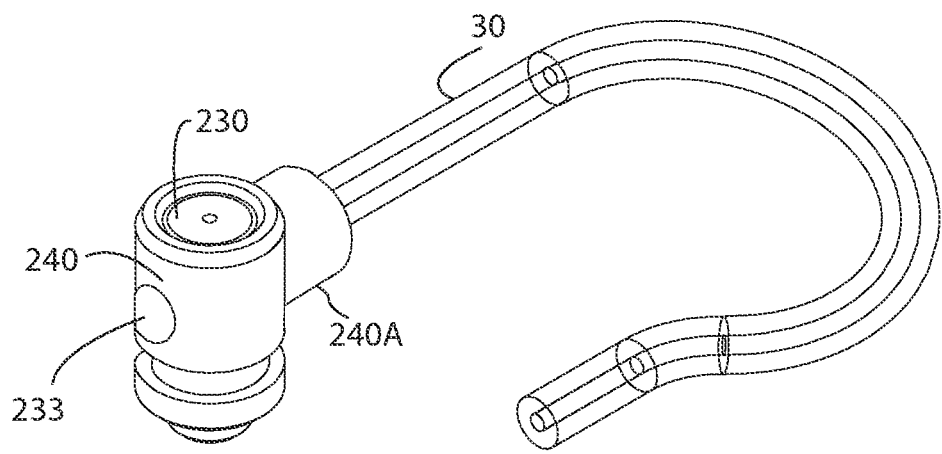
FIG. 5A shows an isometric view of a manifold having a vent, according to a first embodiment of the present invention.
Figure 5B:
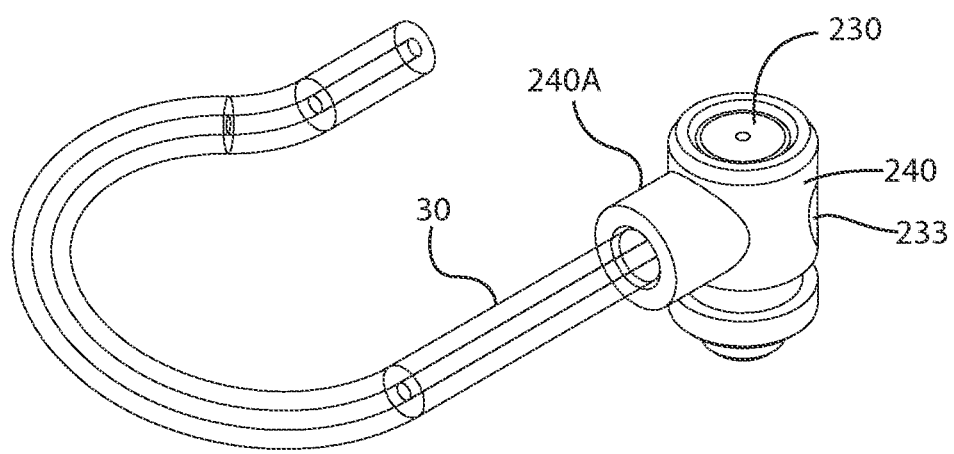
FIG. 5B shows an isometric view of the components shown in FIG. 5A, rotated to show the manifold, manifold intake, and a fluid conduit of the insertion mechanism, according to a first embodiment of the present invention.

The manifold guide 220 may include an upper chamber 222 and a lower chamber 226 separated by a manifold guide ring 228. The upper chamber 222 may have an inner upper chamber 222A, within which the retraction biasing member 216, the clip 218, and the hub 212 may reside during an initial locked stage of operation, and an outer upper chamber 222B, which interfaces with the insertion biasing member 210. In at least one embodiment, the insertion biasing member 210 and the refraction biasing member 216 are springs, preferably compression springs. The hub 212 may be engageably connected to a proximal end of needle 214, such that displacement or axial translation of the hub 212 causes related motion of the needle 214. FIGS. 5A and 5B show isometric views of the fluid conduit 30 connected to the manifold 240 at the manifold intake 240A. FIGS. 5A and 5B show an embodiment of the present invention in which the membrane 233 is located in a portion of the manifold 240 substantially opposite the manifold intake 240A; however, the membrane could be located in any number of positions within the manifold 240. Septum 230 closes the top portion of the manifold 240 from the environment and/or the inside of the pump housing, while permitting a pass-through for the needle or trocar.

As used herein, "needle" is intended to refer to a variety of needles including but not limited to conventional hollow needles, such as a rigid hollow steel needles, and solid core needles more commonly referred to as a "trocars." In a preferred embodiment, the needle is a 27 gauge solid core trocar and in other embodiments, the needle may be any size needle suitable to insert the cannula for the type of drug and drug administration (e.g., subcutaneous, intramuscular, intradermal, etc.) intended. Upon assembly, the proximal end of needle 214 is maintained in fixed contact with hub 212, while the remainder of needle 214 is permitted to pass-through retraction biasing member 216, an aperture of clip 218, and manifold guide 220. The needle 214 may further pass-through septum 230, cannula 234, manifold 240 through manifold header 242, sterile boot 250, and base 252 through base opening 252A. Septum 230, cannula 234, and manifold 240 may reside within lower chamber 226 of manifold guide 220 and within sterile boot 250 until operation of the insertion mechanism. In this position, the cannula 234 may reside over a distal portion of the needle 214 and held in place within the manifold header 242 of manifold 240 by a ferrule 232. Ferrule 232 ensures that cannula 234 remains substantially fixed and in sealed engagement within the manifold 240 to, for example, maintain the sterility of the manifold header 242 until operation of the device. As described above, the ferrule 232 may also function as a restriction or occlusion element to restrict, at least partially, the flow of liquid fluid from the manifold 240 through the cannula 234. Similarly, septum 230 resides substantially fixed and in sealed engagement within the upper portion of the manifold 240 to maintain the sterility of the manifold header 242. These aspects and components may be more clearly visible in the cross-sectional view shown in FIG. 6A.

As would be appreciated by one having ordinary skill in the art, the restriction of fluid flow from the manifold header to the user through the cannula may be adjusted to reach the desired fluid flow characteristics. In at least one embodiment, the fluid flow is substantially entirely prevented until it is desirable and permitted by the removal of the restriction. In other embodiments, however, the restriction (e.g., the needle, the plug, or other occlusion element that prevents or reduces fluid flow) does not entirely prevent fluid flow but instead may be used to reduce or meter the fluid flow through the cannula. This may be desirable, for example, when the fluid flow is initially low volume and then increased at a later time as operation of the device progresses. Similarly, one or more restrictions or occlusion elements may be utilized separately or concurrently. For example, as described further herein, the ferrule may be utilized to restrict fluid flow from the manifold through the cannula to the user.

As described above with reference to FIG. 3A, and detailed further below with reference to FIGS. 4A-4B and 6A-6F, the insertion mechanism having a vented fluid pathway may utilize a single insertion biasing member 210. In an alternative embodiment of the insertion mechanism having a vented fluid pathway, as shown in FIG. 3B, the insertion mechanism 2000 may include two insertion biasing members 2210 A, B. Insertion mechanism 2000 further includes insertion mechanism housing 2202 (shown in transparent view), manifold guide 2220, sterile boot 2250, base 2252, and other components similar to those described above with reference to insertion mechanism 200. In the two insertion biasing members embodiment of the insertion mechanism shown in FIG. 3B, manifold guide ring includes two circular platforms upon which insertion biasing member 2210 A, B may bear. Insertion mechanism 2000 may function identically to insertion mechanism 200, but may provide additional insertion force and/or facilitate different packaging configurations through the use of multiple insertion biasing members 2210 A, B. The components and functions of the insertion mechanisms will be described further herein with the understanding that similar or identical components may be utilized for insertion mechanism 200, insertion mechanism 2000, and all reasonably understood variations thereof. Regardless of the single or multiple insertion biasing member configuration, the insertion mechanisms of the present invention incorporate a vented fluid pathway capable of permitting priming (e.g., evacuation or expulsion of the gaseous fluid) of the drug container, the fluid conduit, and manifold prior to delivery of the drug fluid to the patient. This is enabled, at least in part, by the location of the membrane 233 in the manifold 240 and the function of the insertion mechanism 200 during the insertion and refraction stages of operation.

Figure 6A:
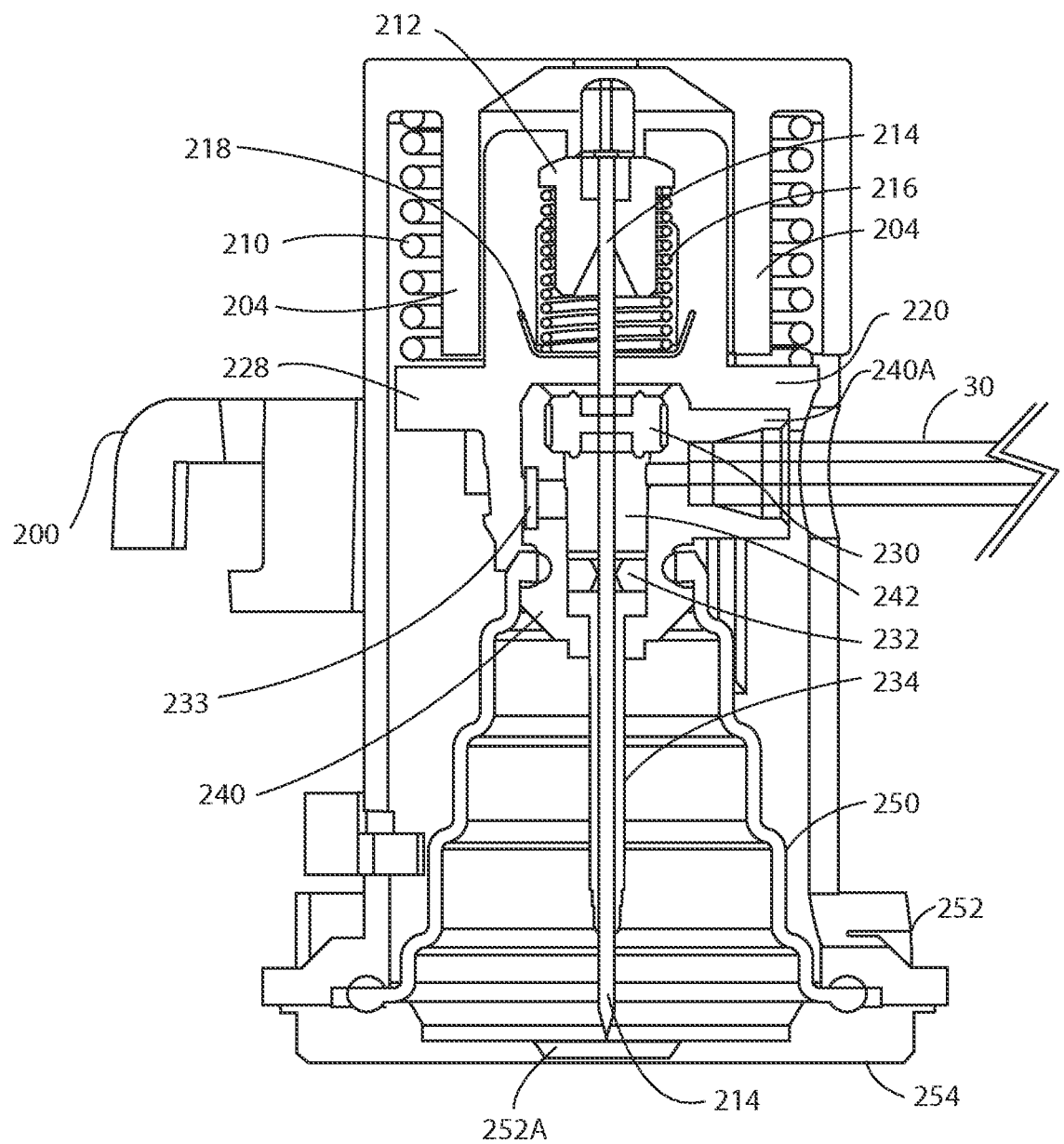
FIG. 6A shows a cross-sectional view of an insertion mechanism having a vented fluid pathway, according to a first embodiment of the present invention, in a locked and ready to use stage.

The operation of the insertion mechanism having a vented fluid pathway is described herein with reference to the above components, in view of FIGS. 6A-6F. FIG. 6A shows a cross-sectional view of the insertion mechanism 200 having a vented fluid pathway, according to at least one embodiment of the present invention, in a locked and ready to use stage. In this initial configuration, insertion biasing member 210 and retraction biasing member 216 are each retained in their compressed, energized states. As shown, the needle 214 may pass through an aperture of clip 218 and manifold guide 220 into septum 230 and manifold 240. Septum 230 resides within manifold 240. Manifold 240 further includes a manifold intake 240A at which the fluid conduit 30 may be connected. This connection is such that the sterility is maintained from the drug container 50 of the drive mechanism 100, through the fluid pathway connection 300 and the fluid conduit 30, into sterile manifold header 242 of manifold 240 and sterile boot 250 to maintain the sterility of the needle 214, cannula 234, and the fluid pathway until insertion into the user for drug delivery. The fluid conduit 30 connects the fluid path from the drug container 50 (visible in FIG. 1B) to the insertion mechanism 200 at manifold intake 240A and into manifold header 242. As described earlier, septum 230 closes the upper portion of the manifold 240 while allowing the needle 214 to pass through it. Another opening from the manifold 240 is at least temporarily blocked by the needle 214 as it resides within the cannula 234, and/or by another occlusion element such as the ferrule 232, prior to operation of the insertion mechanism 200. The only remaining opening from manifold 240 is blocked by membrane 233. As would be readily understood by an ordinarily skilled artisan, membrane 233 may be any number of permeable or semi-permeable membranes which are capable of permitting passage of gaseous fluids while prohibiting passage through the membrane 233 of liquid fluids. In at least one embodiment of the present invention, this is accomplished by utilizing a permeable membrane, such as a hydrophobic permeable membrane, that is permeable to a gaseous fluid but not a liquid fluid, such as the liquid drug treatment. In at least one embodiment of the present invention, it may be beneficial to utilize a permeable membrane that is also a sterile barrier. For example, the membrane 233 may be a polymeric filter made of polyethylene terephthalate (PET) or polytetrafluoroethylene (PTFE), a number of types of styrene, and/or a high-density polyethylene fiber (such as that sold under the trade name TYVEK by DuPont), among many other types of suitable medical-grade gas filtering membranes. Accordingly, because the desired fluid pathway from the manifold 240 to the user through the cannula 234 is blocked by the needle 214, the only available pathway for any gaseous fluid is through the membrane 233.

Figure 6B:
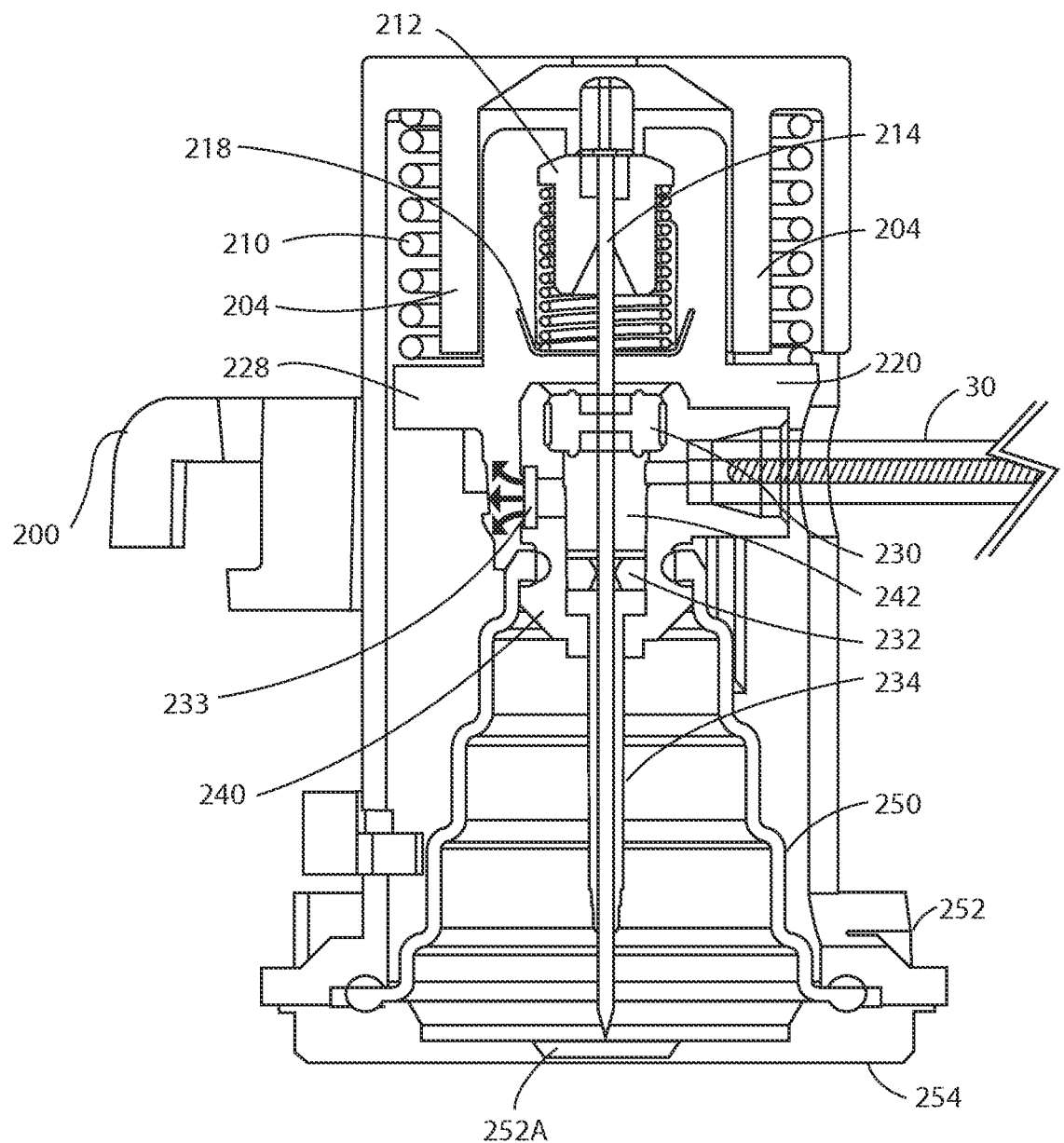
FIG. 6B shows a cross-sectional view of an insertion mechanism having a vented fluid pathway, according to a first embodiment of the present invention, as fluid passes through a conduit and into the manifold.
Figure 6C:
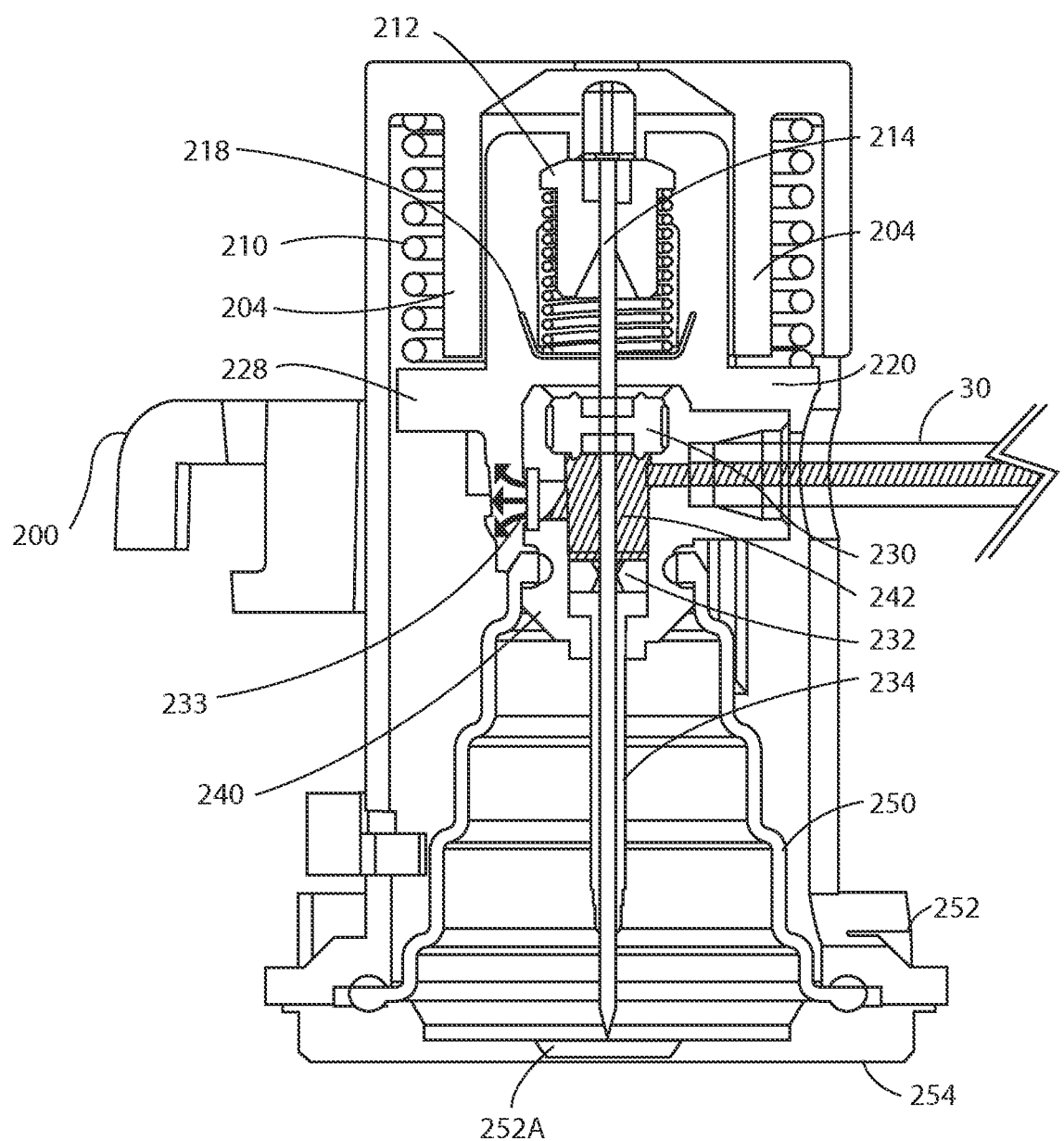
FIG. 6C shows a cross-sectional view of an insertion mechanism having a vented fluid pathway, according to a first embodiment of the present invention, as fluid fills the manifold and gas is pushed through the permeable membrane.
Figure 6D:
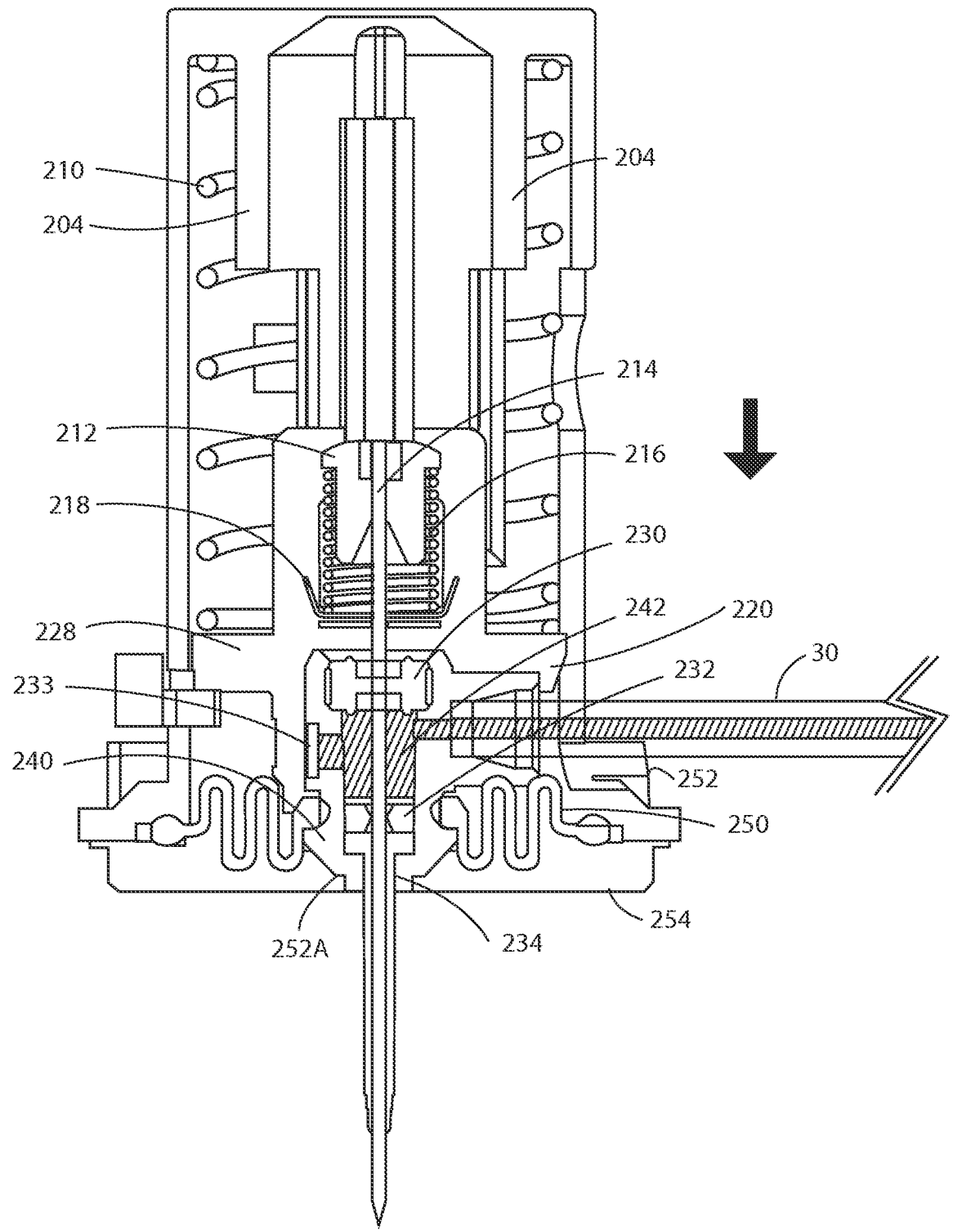
FIG. 6D shows a cross-sectional view of an insertion mechanism having a vented fluid pathway, according to a first embodiment of the present invention, in an unlocked and inserted stage.

As shown in FIG. 6B, as the drug pump is activated and liquid drug fluid (shown as a hatched area) is permitted to pass through the fluid conduit 30, any gaseous fluid in the fluid pathway is caused to enter into the manifold header 242 of the manifold 240. As the pressure of the liquid drug fluid continues to build in the fluid conduit 30, it pushes the gaseous fluid out of the manifold header 242 through the membrane 233 (shown as solid arrows). As stated above, this is possible because the fluid pathway to the user through the cannula 234 remains blocked by the needle 214. FIG. 6C shows a cross-sectional view of an insertion mechanism having a vented fluid pathway as liquid drug fluid fills the manifold and gaseous fluid is substantially fully pushed through the permeable membrane (as shown by the hatched area nearly reaching the membrane 233 and filling the entire manifold header 242). Through the stages of operation of the insertion mechanism having a vented fluid pathway shown in FIGS. 6A-6C, the needle 214 remains at substantially a first position, e.g., a blocking position, within the insertion mechanism 200. In this first position, the needle 214 blocks the fluid pathway through the cannula 234 to the user. As the drug container, fluid conduit 30, and manifold header 242 are vented of gaseous fluid, such as air or inert gas, the needle insertion mechanism may be unlocked and activated to move the needle 214 to a second position, e.g., an inserted position. FIG. 6D shows a cross-sectional view of an insertion mechanism having a vented fluid pathway, according to a first embodiment of the present invention, in an unlocked and inserted stage with the needle 214 in the second position. In this second position, the needle 214 and cannula 234 are inserted (in the direction of the solid arrow in FIG. 6D) into the body of the user.

The timing of the activation of the insertion mechanism 200 to move the needle 214 from the first position to the second position may be coordinated by a timing mechanism controlled by, for example, the power and control system or by a mechanical delay directly from user activation of the drug pump. Additionally or alternatively, a number of sensors may be utilized to identify when the gaseous fluid has been substantially entirely expelled from the fluid pathway and the fluid pathway is primed for delivery of liquid drug fluid to the user. For example, pressure sensors may be utilized to monitor back-pressure (e.g., pressure build-up) in the fluid pathway resulting from the liquid fluid substantially filling the manifold header 242 and expulsion of any gaseous fluid from the drug container, fluid conduit 30, and manifold 240. Similarly, the rate of fluid flow may be actively controlled or passively controlled. For example, in at least one embodiment of the present invention, tubing or other fluid conduits with a controlled diameter or geometry, orifice, or other limiting mechanism may be utilized to control the rate of flow. Such mechanisms may provide means for passive control of the rate of delivery. The orifice or tubing can be used to passively modulate flow when coupled with an induced pressure in the primary drug container, i.e., the pressure exerted by the pump mechanism on the liquid fluid as it is forced out of the primary drug container. In some embodiments, the device may be configured to actively control the flow of delivery by an electrical means, a mechanical means, or a combination of both. For example, one or more solenoids may be utilized to actively control the flow of delivery by closing and/or opening the fluid pathway.

Additionally or alternatively, one or more timing mechanisms may be utilized which are directly coupled to the drive mechanism which subsequently brake or meter the delivery rate or total time to deliver a volume of liquid fluid from the primary drug container. It is to be understood that the mechanisms, methods, and devices of the present invention may be used control the total time of drug delivery, the static rate of delivery during the entire time of delivery, a dynamic rate of delivery during any interval period of the entire time of delivery, or any combination of the above. For example, the device may be configured to provide drug delivery which, start to finish, completes in a specified amount of time, for example 5 minutes. This could be configured to be irrespective of the rate of delivery, such that: (a) the rate of delivery may be initially high and then later low; (b) a constant rate during the entire time of delivery; or (c) constant rates that vary at different intervals within the entire time of delivery; (d) or any combination of these delivery methodologies. The insertion of the blocking needle and activation of the liquid fluid (e.g., drug treatment) flow may similarly be controlled to ensure there is enough time for the system to vent (i.e., prime the fluid pathway) prior to introduction of the liquid fluid to the user. After substantially all of the gaseous fluid has been expelled from the drug container, fluid conduit, and manifold, and the insertion mechanism has moved the needle from the first position to the second position, the fluid pathway is ready to permit delivery of the drug fluid to the user.

Figure 6E:
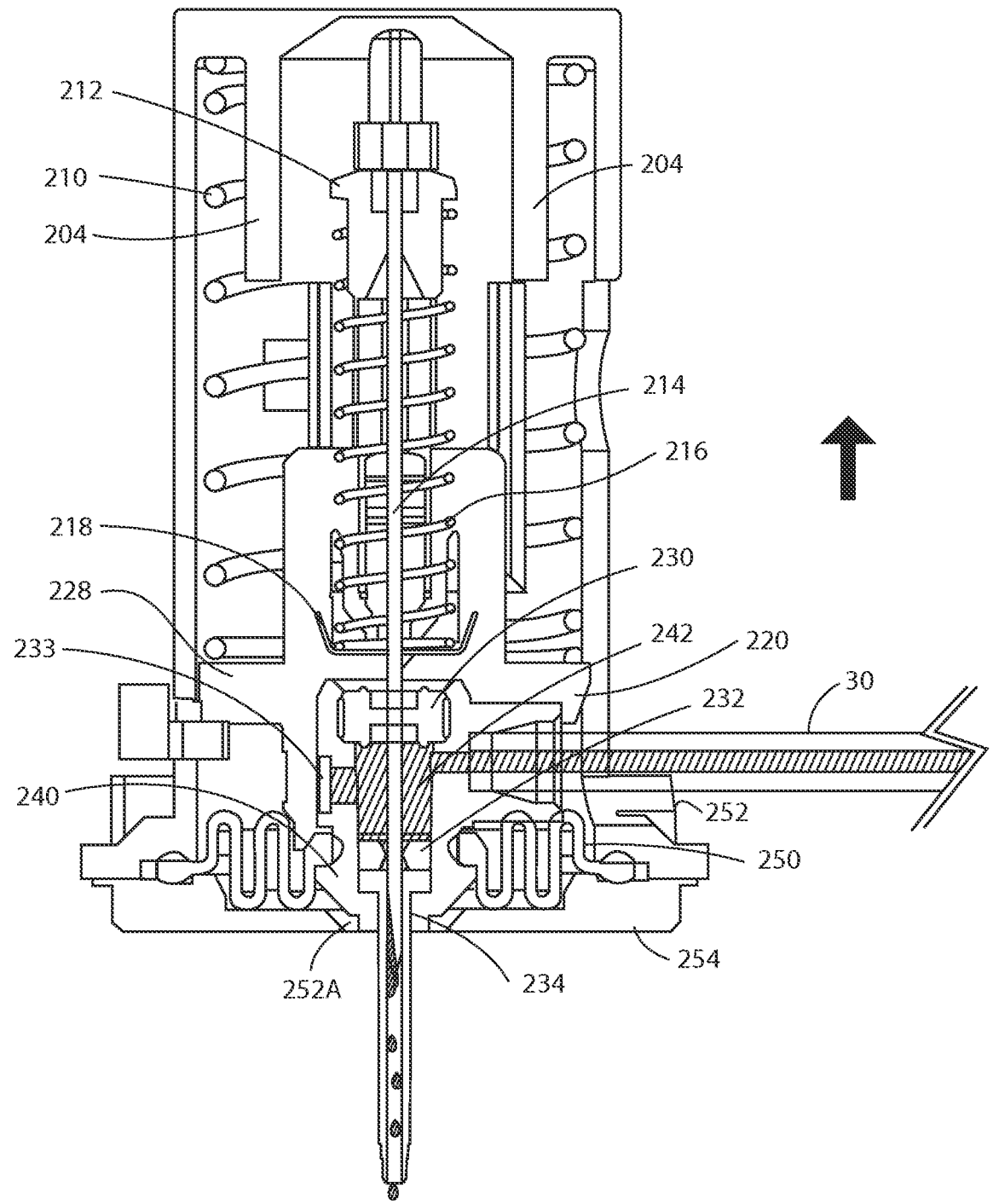
FIG. 6E shows a cross-sectional view of an insertion mechanism having a vented fluid pathway, according to a first embodiment of the present invention, in a partially retracted stage as fluid begins exiting the manifold through the cannula.
Figure 6F:
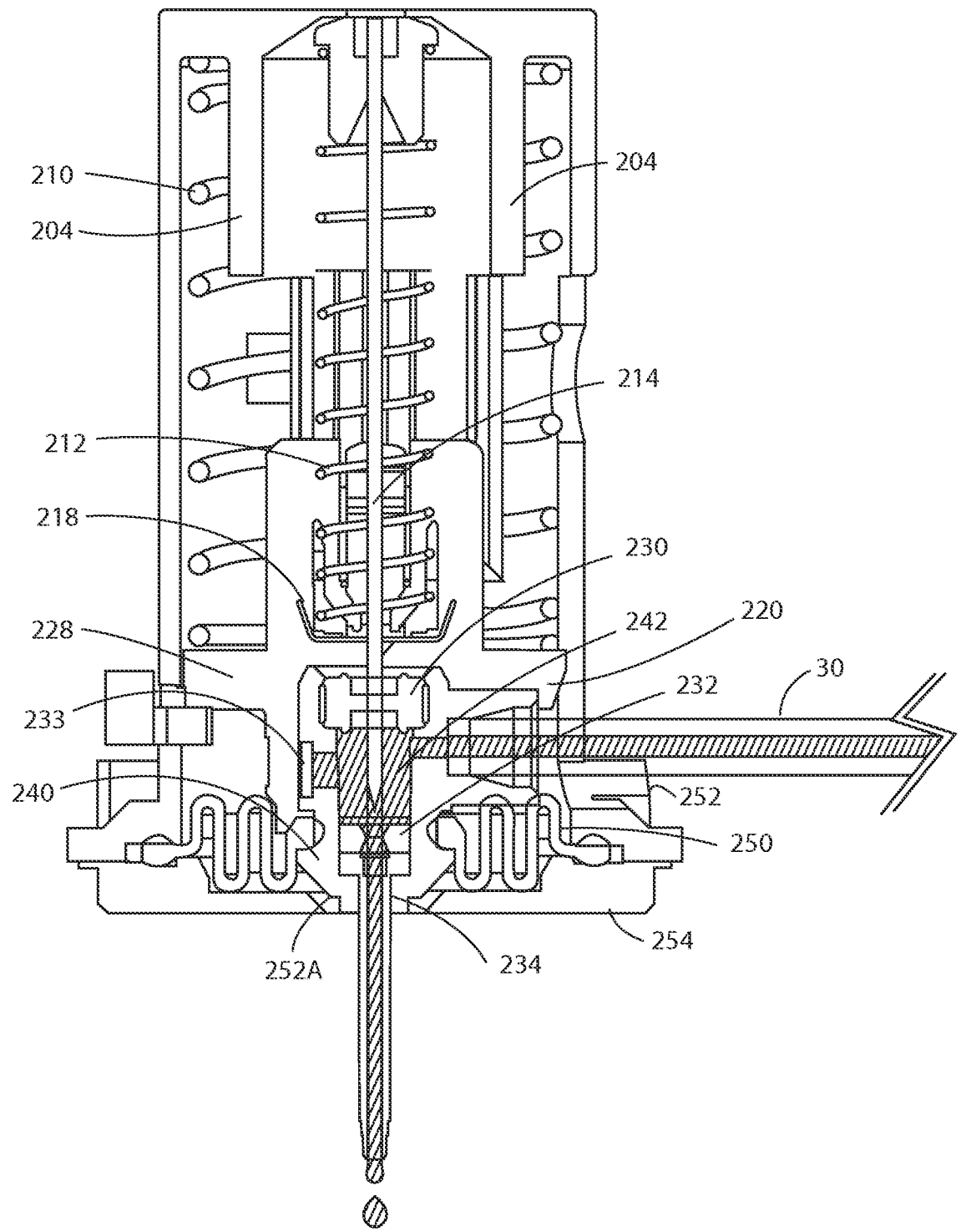
FIG. 6F shows a cross-sectional view of an insertion mechanism having a vented fluid pathway, according to a first embodiment of the present invention, in a retracted stage for drug delivery.

FIG. 6D shows a cross-sectional view of an insertion mechanism in the second, e.g., needle inserted, position. As shown, sterile boot 250 is permitted to collapse as the insertion biasing member 210 expands and inserts the needle 214 and cannula 234 into the body of the user. At this stage, needle 214 is introduced into the body of the user to place the cannula 234 into position for drug delivery. As shown in FIG. 6E, upon needle 214 and cannula 234 insertion by operation of the insertion biasing member 210 as described above, the needle 214 is retracted back (i.e., axially translated in the proximal direction) into the housing of the insertion mechanism 200. Manifold guide 220 and clip 218 (shown in FIGS. 4A and 4B), and guide protrusions 204, are dimensioned such that, as the manifold 240 substantially bottoms-out on base 252, i.e., reaches its full axial translation in the distal direction, the clip 218 escapes the guide protrusions 204 and is permitted to flex outwards to disengage from hub 212. Upon such disengagement, retraction biasing member 216 is permitted to expand axially in the proximal direction (i.e., in the direction of solid arrow in FIG. 6E) from its initial compressed, energized state. A suitable lockout mechanism prevents axial translation in the proximal direction of the manifold guide 220 and insertion mechanism components that are distal to (i.e., below) the manifold guide ring 228. Expansion of the retraction biasing member 216 translates hub 212, and needle 214 to which it is connected, axially in the proximal direction from the second position to a third position, i.e., a needle retracted position. Ferrule 232 retains cannula 234 inserted within the body of the user through base opening 252A. Upon retraction of the needle 214 from cannula 234, the fluid pathway from manifold header 242 to the body of the user through the cannula 234 is opened and fluid may begin to pass-through the cannula 234, as shown in FIG. 6E. As the fluid pathway connection to the user is completed, the fluid drug treatment is forced from the drug container through the fluid pathway connection and the sterile fluid conduit into the manifold header 242 and through the cannula 234 for delivery into the body of the user. Accordingly, activation of the insertion mechanism inserts the needle 214 and cannula 234 into the body of the user from a first position to a second position, and sequentially retracts the needle 214 from the second position to a third position, i.e., the retracted position, while maintaining the cannula 234 in fluid communication with the body of the user. FIG. 6F shows a cross-sectional view of an insertion mechanism having a vented fluid pathway in the third retracted position for drug delivery. As shown, the needle 214 does not need to be fully retracted from septum 230, though this may be desirable and permissible in other embodiments of the present invention, so long as the fluid pathway through the cannula 234 to the body of the user is opened. At the end of the drug dose delivery, the cannula 234 may be removed from the body of the user by removal of the drug pump from contact with the user.

In another embodiment of the present invention, the fluid pathway may be blocked by a plug, stopper, cork, or other removable occlusion element. For example, during the venting stage a removable plug or stopper may be utilized to block the portion of the fluid pathway that is in connection with the user. The plug, stopper, or other similar occlusion element is retracted or removed from the pathway after venting has substantially completed, enabling the liquid fluid to be delivered into the user. This may be desirable in configurations which use, for example, a rigid needle in fluid connection with the patient. For example, in at least one embodiment of the present invention, a rigid hollow needle may be utilized in place of the solid core trocar needle described above. In such an embodiment, the needle and, optionally, a cannula are inserted from a first position to a second position into the user. The needle and optional cannula are then retained within the body of the user. Instead of retracting the needle, the needle remains in the second position and a plug, stopper, or other similar occlusion element is removed or retracted from the needle to a third position, after the venting stage, to open the fluid pathway for drug delivery to the user.

Figure 7A:
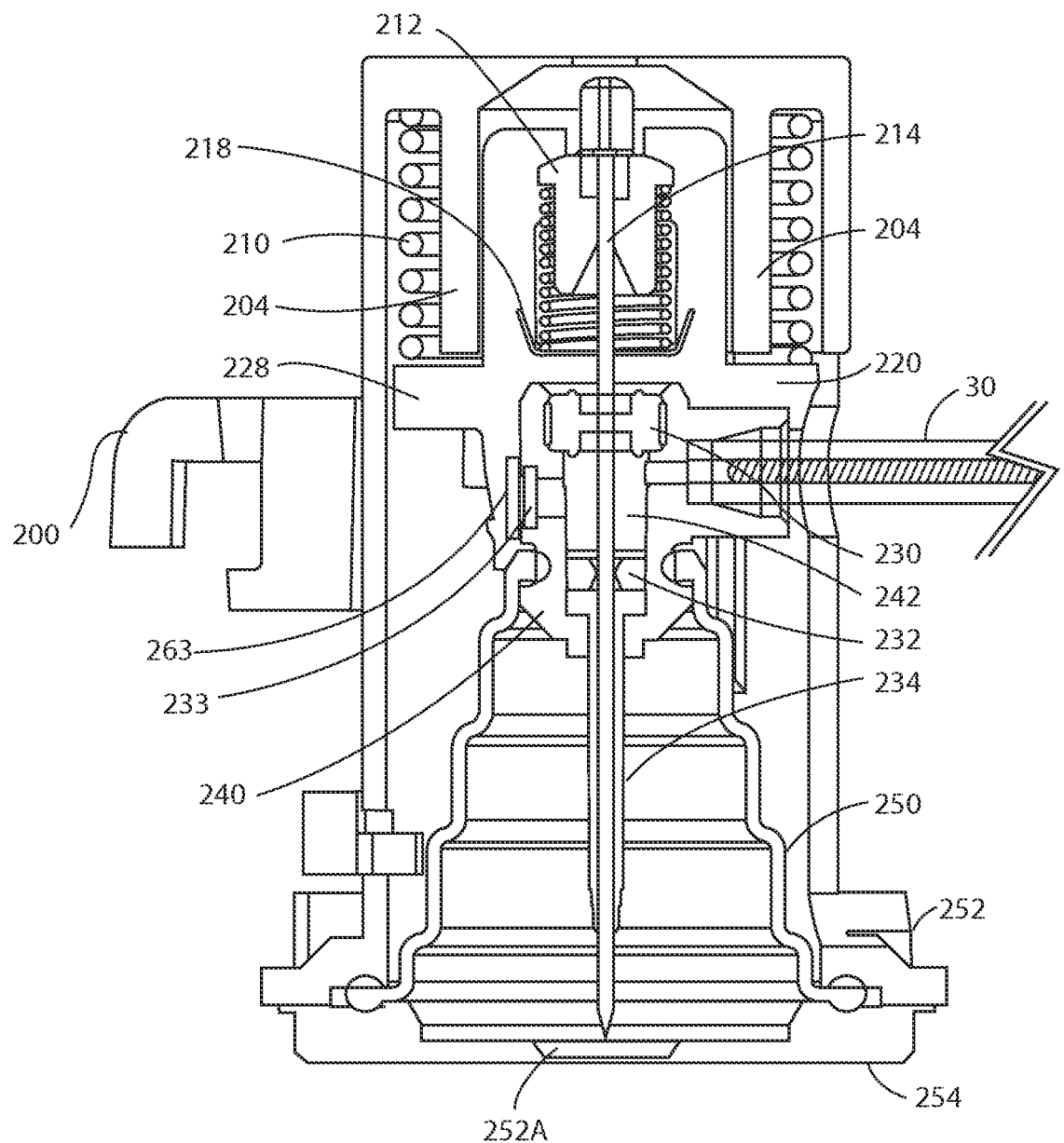
FIGS. 7A-7C show cross-sectional views of an insertion mechanism having a vented fluid pathway, according to another embodiment of the present invention, as it progresses through the various stages of insertion, venting, and drug delivery.
Figure 7B:
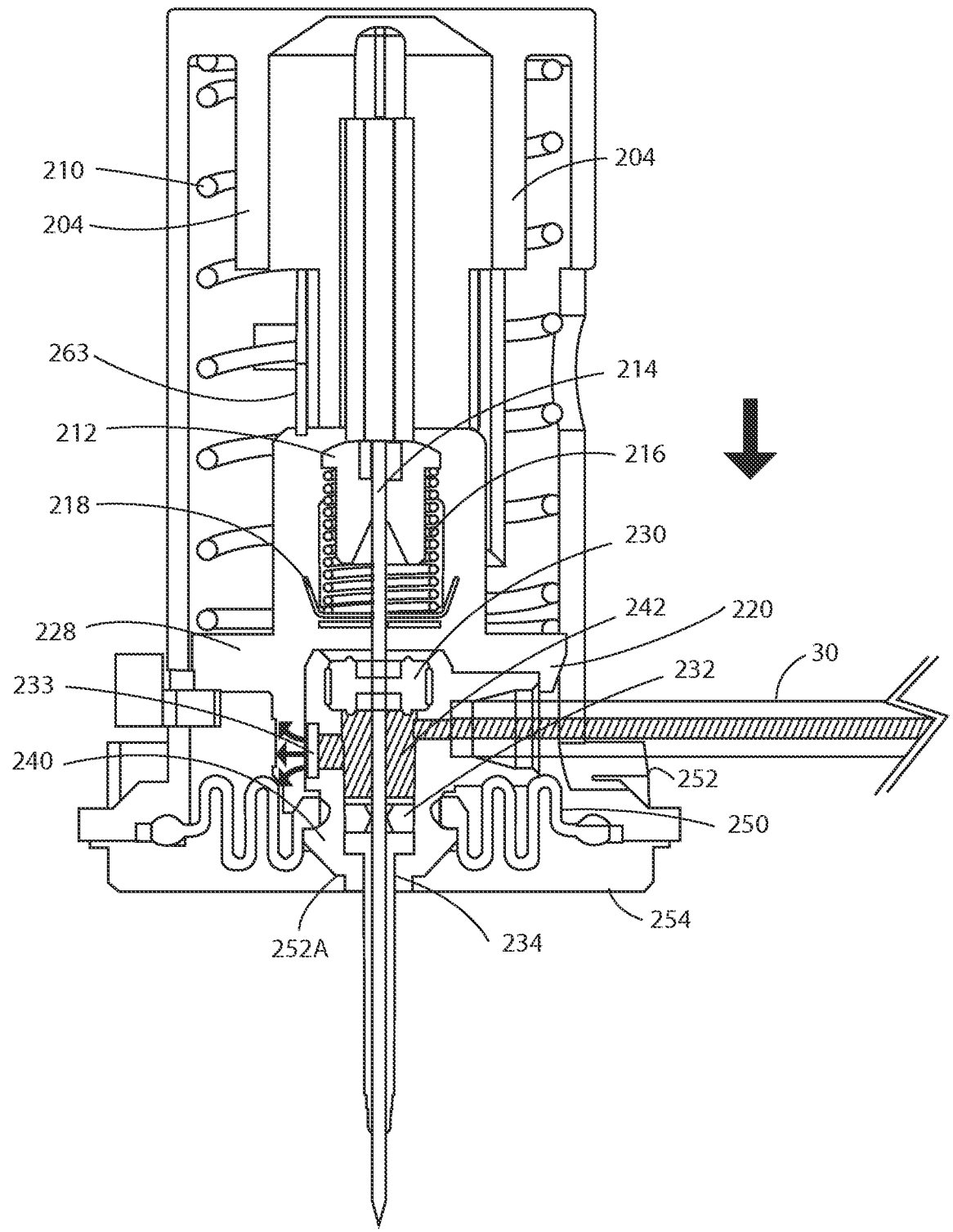
Figure 7C:
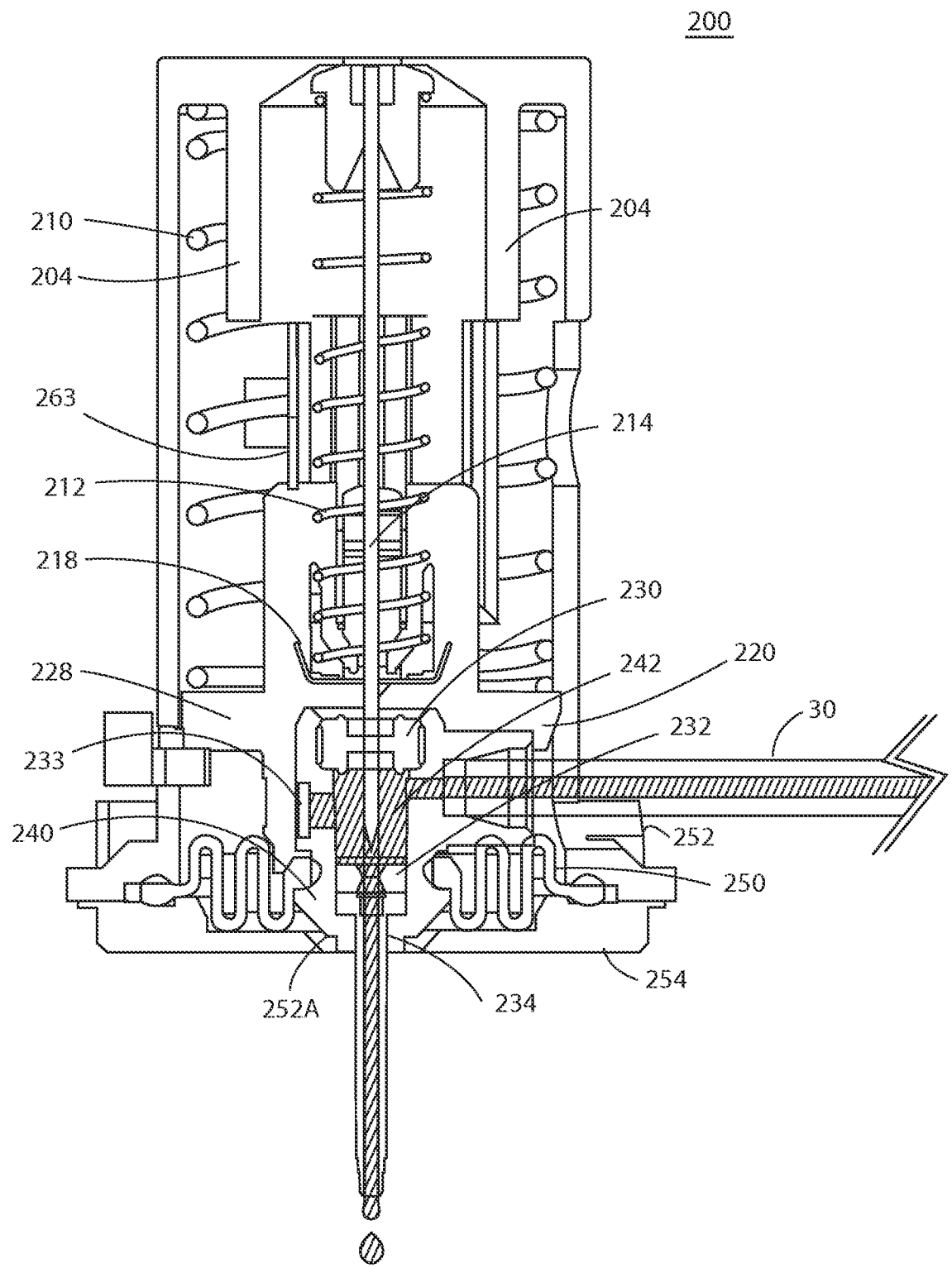

A method of operating an insertion mechanism having a vented fluid pathway according to the present invention includes: initially maintaining a needle in a first position within a cannula and thereby blocking fluid passage from a manifold header of a manifold through the cannula; activating the flow of liquid drug fluid from a drug container through a fluid conduit to the manifold header of the manifold; venting a gaseous fluid through a membrane within the manifold while prohibiting passage of the liquid drug fluid through the membrane; activating an insertion biasing member to translate the needle and the cannula from the first position to a second position within a body of a user; and activating a retraction biasing member to translate the needle from the second position to a third position, wherein the third position permits passage of the liquid drug fluid from the manifold header of the manifold through the cannula and into the body of the user. In at least one embodiment of the present invention, the step of activating an insertion biasing member to translate the needle and the cannula from the first position to a second position occurs after the step of venting a gaseous fluid through a membrane within the manifold. In an alternative embodiment, however, the step of activating an insertion biasing member to translate the needle and the cannula from the first position to a second position may occur before the step of venting a gaseous fluid through a membrane within the manifold such that venting through the membrane is permitted only once the needle is in the second position. Such an embodiment is shown in FIGS. 7A-7C. In this embodiment, the fluid pressure in the fluid conduit may build and force any gaseous fluid in the fluid pathway into the manifold for venting through the membrane, as shown in FIG. 7A. Once the fluid pathway has been suitably pressurized in this way, the insertion biasing member may be triggered to translate the needle and the cannula from the first position to a second position, thereby opening, uncovering, or otherwise unblocking the membrane to evacuate the gaseous fluid from the manifold. This is visible in FIG. 7B. A blocking or covering element 263 such as a sleeve, cover, sheath, or other similar component may be utilized outside of the manifold adjacent the membrane to initially cover or block the membrane in the first position and to uncover or unblock the membrane in the second position to permit venting, as shown in FIG. 7C. In either embodiment, however, passage of the liquid drug fluid is permitted to occur only after the venting step and upon translation of the needle from the second position to a third position, wherein the third position permits passage of the liquid drug fluid from the manifold the manifold header of the manifold through the cannula and into the body of the user. The method may further include, prior to the step of activating a retraction biasing member to translate the needle from the second position to a third position, the step of: measuring by a sensor the substantial completion of venting the gaseous fluid through the membrane.

Certain optional standard components or variations of insertion mechanism 200 or drug delivery pump 10 are contemplated while remaining within the breadth and scope of the present invention. For example, upper or lower housings may optionally contain one or more transparent or translucent windows 18, as shown in FIGS. 1A-1C, to enable the user to view the operation of the drug delivery pump 10 or verify that drug dose has completed. Additionally, the drug delivery pump 10 may contain an adhesive patch 26 and a patch liner 28 on the bottom surface of the housing 12. The adhesive patch 26 may be utilized to adhere the drug delivery pump 10 to the body of the user for delivery of the drug dose. As would be readily understood by one having ordinary skill in the art, the adhesive patch 26 may have an adhesive surface for adhesion of the drug pump to the body of the user. The adhesive surface of the adhesive patch 26 may initially be covered by a non-adhesive patch liner 28, which is removed from the adhesive patch 26 prior to placement of the drug delivery pump 10 in contact with the body of the user. Adhesive patch 26 may optionally include a protective shroud that prevents actuation of the optional on-body sensor 24 and covers base opening 252A. Removal of the patch liner 28 may remove the protective shroud or the protective shroud may be removed separately. Removal of the patch liner 28 may further remove the sealing membrane 254 of the insertion mechanism 200, opening the insertion mechanism to the body of the user for drug delivery.

Similarly, certain components of the present invention may be unified components or separate components while remaining within the breadth and scope of the described embodiments. For example, the membrane is shown as a component of the manifold of the insertion mechanism. The membrane may be a separate component or may comprise a wall of the manifold, as would readily be appreciated by one having ordinary skill in the art. In an alternative embodiment, the membrane may be located at the distal end of the fluid conduit or be a distal portion of the fluid conduit itself. The vent location enabled by the membrane determines the degree to which the system may be primed, however. To reduce dead volume within the fluid pathway and reduce the gaseous fluid that may be delivered to the user, it may be desirable to have the membrane as close as possible to the end of the fluid pathway. Accordingly, the membrane is preferably an integrated aspect of the manifold of the needle insertion mechanism. Such standard components and functional variations would be appreciated by one having ordinary skill in the art and are, accordingly, within the breadth and scope of the present invention.

Assembly and/or manufacturing of insertion mechanism 200, drug delivery pump 10, or any of the individual components may utilize a number of known materials and methodologies in the art. For example, a number of known cleaning fluids such as isopropyl alcohol may be used to clean the components and/or the devices. A number of known adhesives or glues may similarly be employed in the manufacturing process. Additionally, known siliconization fluids and processes may be employed during the manufacture of the novel components and devices. Furthermore, known sterilization processes may be employed at one or more of the manufacturing or assembly stages to ensure the sterility of the final product.

Throughout the specification, the aim has been to describe the preferred embodiments of the invention without limiting the invention to any one embodiment or specific collection of features. Various changes and modifications may be made to the embodiments described and illustrated without departing from the present invention. The disclosure of each patent and scientific document, computer program and algorithm referred to in this specification is incorporated by reference in its entirety.

What is claimed is:

1. An insertion mechanism having a vented fluid pathway, comprising:
   one or more insertion biasing members;
   a hub;
   a solid core needle coupled to the hub;
   a retraction biasing member configured to selectively retract the needle; and
   a manifold having a septum configured to allow the needle to pass through it, a cannula, a manifold intake, a first opening, a gas-permeable membrane disposed across the first opening and a second opening through which the cannula extends, wherein:
      the annular space within the manifold between the septum, the cannula, the manifold intake, and the membrane defines a manifold header, which is closed by the septum, the gas-permeable membrane and the needle when the needle resides within the cannula and the manifold intake is connected to a drug container; and
      the manifold is configured to vent a gaseous fluid through the gas-permeable membrane outside a body of a user, and fill with a liquid fluid for delivery to the user through the cannula.

2. The insertion mechanism of claim 1, wherein the manifold intake is capable of connection with a fluid conduit.

3. The insertion mechanism of claim 1, wherein the insertion mechanism is configured to be internally mounted within a drug delivery pump.

4. The insertion mechanism of claim 1, wherein the insertion mechanism is configured to be externally tethered to a drug delivery pump by a conduit.

5. The insertion mechanism of claim 1, wherein the insertion mechanism comprises two insertion biasing members.

6. The insertion mechanism of claim 1, wherein the gas-permeable membrane comprises polyethylene terephthalate, polytetrafluoroethylene, one or more styrenes, polyethylene fiber, or any combination thereof, wherein the gas-permeable permeable membrane is capable of permitting passage of gaseous fluids but prohibiting passage of liquid fluids.

7. The insertion mechanism of claim 1, wherein the gas-permeable membrane is an integrated portion of the manifold.

8. The insertion mechanism of claim 1, further comprising a sensor.

9. The insertion mechanism of claim 8, wherein the sensor is selected from the group consisting of pressure sensors, fluid sensors, optical sensors, mechanical sensors, electrical sensors, and electro-mechanical sensors, and the combinations thereof.

10. The insertion mechanism of claim 1, further comprising a ferrule which maintains the cannula in a fixed and sealed position within the manifold.

11. The insertion mechanism of claim 1, further comprising a blocking element outside of the manifold, wherein the blocking element is a cover, sheath, or sleeve.

12. A drug delivery pump comprising a housing and an assembly platform, upon which an activation mechanism, a drive mechanism, a fluid pathway connection, a power and control system, and an insertion mechanism having a vented fluid pathway may be mounted, the drug delivery pump further comprising an insertion mechanism having a vented fluid pathway comprising:
one or more insertion biasing members;
a hub;
a solid core needle coupled to the hub;
a retraction biasing member configured to selectively retract the needle; and
a manifold having a septum configured to allow the needle to pass through it, a cannula, a manifold intake, a first opening, a gas-permeable membrane disposed across the first opening and a second opening through which the cannula extends, wherein:
the annular space within the manifold between the septum, the cannula, the manifold intake, and the membrane defines a manifold header, which is closed by the septum, the gas-permeable membrane and the needle when the needle resides within the cannula and the manifold intake is connected to a drug container; and
the manifold is configured to vent a gaseous fluid through the gas-permeable membrane outside a body of a user, and fill with a liquid fluid for delivery to the user through the cannula.

13. The drug delivery pump of claim 12, wherein the manifold intake is capable of connection with a fluid conduit.

14. The drug delivery pump of claim 12, wherein the insertion mechanism is configured to be internally mounted within a drug delivery pump.

15. The drug delivery pump of claim 12, wherein the insertion mechanism is configured to be externally tethered to a drug delivery pump by a conduit.

16. The drug delivery pump of claim 12, wherein the insertion mechanism comprises two insertion biasing members.

17. The drug delivery pump of claim 12, wherein the gas-permeable membrane comprises polyethylene terephthalate, polytetrafluoroethylene, one or more styrenes, polyethylene fiber, or any combination thereof, wherein the gas-permeable membrane is capable of permitting passage of gaseous fluids but prohibiting passage of liquid fluids.

18. The drug delivery pump of claim 12, wherein the gas-permeable membrane is an integrated portion of the manifold.

* * * * *